United States Patent
Alam et al.

(10) Patent No.: US 10,266,648 B2
(45) Date of Patent: Apr. 23, 2019

(54) FLAME RETARDANT RESIN COMPOSITION

(71) Applicant: Momentive Performance Materials Inc., Waterford, NY (US)

(72) Inventors: Samim Alam, Tarrytown, NY (US); Koji Suenaga, Gunma (JP); Roy Rojas-Wahl, Teaneck, NJ (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 15/634,582

(22) Filed: Jun. 27, 2017

(65) Prior Publication Data

US 2017/0369644 A1    Dec. 28, 2017

Related U.S. Application Data

(60) Provisional application No. 62/355,093, filed on Jun. 27, 2016, provisional application No. 62/452,582, filed on Jan. 31, 2017.

(51) Int. Cl.
| | | |
|---|---|---|
| C08L 83/00 | (2006.01) |
| C08G 64/42 | (2006.01) |
| C08F 8/42 | (2006.01) |
| C08G 69/48 | (2006.01) |
| C08G 75/20 | (2016.01) |
| C08G 77/38 | (2006.01) |
| C08L 69/00 | (2006.01) |
| C08G 77/50 | (2006.01) |
| C08G 77/00 | (2006.01) |
| C07F 7/08 | (2006.01) |
| C08K 5/5419 | (2006.01) |
| C08K 5/5425 | (2006.01) |

(52) U.S. Cl.
CPC ............ *C08G 64/42* (2013.01); *C07F 7/0838* (2013.01); *C08F 8/42* (2013.01); *C08G 69/48* (2013.01); *C08G 75/20* (2013.01); *C08G 77/38* (2013.01); *C08G 77/50* (2013.01); *C08G 77/80* (2013.01); *C08K 5/5419* (2013.01); *C08K 5/5425* (2013.01); *C08L 69/00* (2013.01); *C08L 83/00* (2013.01); *C08L 2201/02* (2013.01)

(58) Field of Classification Search
None
See application file for complete search history.

(56) References Cited

U.S. PATENT DOCUMENTS

| | | | | |
|---|---|---|---|---|
| 2,714,099 A * | 7/1955 | Weyenberg | ............ | C08G 77/00 526/279 |
| 2,768,149 A * | 10/1956 | Miller | ............ | C08G 77/16 524/863 |
| 2,934,464 A * | 4/1960 | Hoffman | ............ | C08J 5/24 156/329 |
| 3,234,180 A * | 2/1966 | Wu | ............ | C08G 77/12 528/14 |
| 3,297,632 A * | 1/1967 | Wu | ............ | C08G 77/04 528/12 |
| 3,310,526 A * | 3/1967 | Sporck | ............ | C07F 7/0874 528/12 |
| 3,775,452 A | 11/1973 | Karstedt | | |
| 4,197,384 A * | 4/1980 | Bialous | ............ | C08K 5/5415 524/114 |
| 4,828,739 A * | 5/1989 | Satoh | ............ | C10M 107/50 508/208 |
| 4,954,549 A * | 9/1990 | Lewis | ............ | C08K 5/5403 524/264 |
| 4,996,255 A | 2/1991 | Davis et al. | | |
| 5,955,542 A | 9/1999 | Davis et al. | | |
| 6,184,312 B1 | 2/2001 | Yamamoto et al. | | |
| 7,868,118 B2 | 1/2011 | Verbruggen et al. | | |
| 8,263,720 B1 | 9/2012 | Salamone et al. | | |
| 8,299,181 B2 | 10/2012 | Weller et al. | | |
| 9,006,322 B1 * | 4/2015 | Wilczek | ............ | C08L 59/02 524/266 |
| 9,422,315 B2 | 8/2016 | Suenaga et al. | | |
| 2003/0162929 A1 | 8/2003 | Verbruggen et al. | | |
| 2005/0254003 A1 | 11/2005 | Jani et al. | | |
| 2007/0142551 A1 * | 6/2007 | Kunzler | ............ | C08G 77/50 525/100 |
| 2012/0071678 A1 * | 3/2012 | Arkles | ............ | C07F 7/0809 556/11 |
| 2015/0017455 A1 * | 1/2015 | MacGregor | ............ | C08L 83/04 428/447 |
| 2015/0166708 A1 | 6/2015 | Alam et al. | | |
| 2015/0274895 A1 * | 10/2015 | Okawa | ............ | H01L 33/56 523/210 |
| 2016/0159829 A1 | 6/2016 | Suenaga et al. | | |
| 2017/0058145 A1 * | 3/2017 | Rhodes | ............ | C08F 232/00 |

FOREIGN PATENT DOCUMENTS

| EP | 0415072 A2 | 7/1990 | | |
|---|---|---|---|---|
| JP | 49009456 B | * 3/1974 | ............ | C07F 5/02 |
| JP | 2009155381 A | 7/2009 | | |

OTHER PUBLICATIONS

V. S. Chugunov "Synthesis of Some Triphenylmethyl- and Triphenylethylsiloxanes", Institutes of Silicate Chemistry of the Academy of Sciences, USSR, 1956, 1386-1387. (Year: 1956).*
W. Zhou, H. Yang / Thermochimica Acca 452 (2007) 43-48.
Iji et al., "Silicone Derivatives as New Flame Retardants for Aromatic Thermoplastics Used in Electronic Devices"; Polymers for Advanced Technologies 9: 593-600 (1998).
Chrusciel et al., "Modification of Thermoplastics with Reactive Silanes and Siloxanes", retrieved from Internet: URL: http://cdn.intechopen.com/pdfs/34066 on Sep. 5, 2017, p. 156-192.
International Search Report and Written Opinon from PCT/US2017/039498 dated Sep. 19, 2017.

* cited by examiner

*Primary Examiner* — Robert S Loewe
(74) *Attorney, Agent, or Firm* — James C. Abruzzo

(57) ABSTRACT

A flame-retarded resin includes at least one resin for which flame retardant capability is desired and at least one triaryl silicon-containing compound (I) as flame retardant in admixture therewith and/or chemically bonded, e.g., grafted, to the resin.

34 Claims, No Drawings

FLAME RETARDANT RESIN COMPOSITION

CROSS REFERENCE TO RELATED APPLICATION

This application claims the 35 U.S.C. § 120 benefit of provisional U.S. patent application Ser. Nos. 62/355,093, filed Jun. 27, 2016, and 62/452,582, filed Jan. 31, 2017, the entire contents of which are incorporated by reference herein.

FIELD OF THE INVENTION

The present invention relates to silicones and, more particularly, to triaryl containing compounds useful, inter alia, as flame retardants for polymers and to resin compositions for which flame retardant capability is desired.

BACKGROUND INVENTION

For many applications of resins (solid polymers), effective resistance to flame ignition is required. In order to increase the flame retardant properties of various and meet an industry or government standard of flame retardancy for specific polymers, flame retardant additives (organic and inorganic) are commonly admixed therewith and/or chemically bonded thereto in the case of polymer-reactive flame retardants. Organic flame retardants such as halogenated flame retardants, specifically brominated flame retardants, and phosphorus-containing flame retardants are considered to be effective for this purpose.

Inorganic flame retardants are another class of known flame retardant. Usually higher loading of inorganic flame retardants such as aluminum hydroxide, titania, carbon black, zinc oxide, antimony trioxide, etc., are required than that of halogenated flame retardants to achieve the same level of flame retardancy. However, high loading of inorganic flame retardants can negatively affect the optical and mechanical properties of the base polymer. In the case of flame retardant resin compositions containing organophosphorus flame retardant compounds such as triphenyl phosphate (TPP), combustion may tend to produce relatively high levels of smoke.

In many applications such as helmets, bullet proof glass, etc., optical transparency of the molding resin, e.g., polycarbonate at various service temperatures including low temperatures, is an important functional requirement. However, the addition of inorganic flame retardant(s) often reduces the transparency of the host resin.

Polydimethylsiloxane is a popular class of flame retardant for polycarbonate as the combustion products are less toxic than that of halogenated flame retardants. Due to the difference in compatibility between the polycarbonate and the silicone, the incorporation of silicone flame retardant in polycarbonate can reduce the optical transparency and increase haze of the polycarbonate-silicone flame retardant blend.

Therefore, there is a need for an improved flame retardant resin composition which produces less toxic combustion products than those produced by conventional or otherwise known flame retardant resin compositions, e.g., those containing organic halogen- or phosphorus-based flame retardant compounds, while providing improved optical and/or mechanical properties compared with those of known flame retardant resin composition containing inorganic flame retardant compounds.

SUMMARY OF THE INVENTION

In accordance with the present invention, a flame retardant resin composition is provided which comprises (a) at least one resin which does not contain a triarylsiloxy group, i.e., as $Ar_3SiO$— group wherein each Ar independently is an unsubstituted aryl group of from about 6 to about 20 carbon atoms, and (b) at least one triaryl silicon-containing compound of general formula (I):

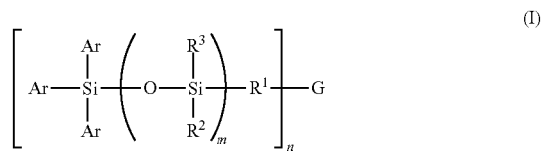

wherein each Ar independently is an unsubstituted aryl group of from about 6 to about 20 carbon atoms or substituted aryl group of from about 6 to about 20 carbon atoms; each $R^2$ and $R^3$ independently is a monovalent hydrocarbon group of from 1 to about 8 carbon atoms; each $R^1$ is independently a divalent saturated or unsaturated hydrocarbon group of from 1 to about 45 carbon atoms, more specifically from 2 to about 30 carbon atoms, still more specifically from 2 to about 20 carbon atoms and most specifically from 2 to about 12 carbon atoms, optionally containing one or more heteroatoms, specifically from 1 to about 20 oxygen, sulfur, silicon and/or nitrogen atoms, and still more specifically from 1 to about 10 oxygen atoms, or a chemical bond; G is hydrogen, a hydroxyl group, an acyclic organic group of from 1 to about 45 carbon atoms, a cyclic organic group of from 3 to about 20 carbon atoms, an acyclic or cyclic silicon-containing organic group such as an acyclic or cyclic silicone group, a triarylsilyloxy group $Ar_3SiO$— wherein Ar is as previously defined, e.g., a $Ph_3SiO$— group, an alkoxysilyl group of the formula —$SiR^4_a(OR^5)_{3-a}$, wherein each occurrence of $R^4$ independently is a monovalent hydrocarbon group of from 1 to about 12 carbon atoms, more specifically from 1 to 4 carbon atoms and still more specifically 1 or 2 carbon atoms, each occurrence of $R^5$ independently is a monovalent hydrocarbon group of from 1 to about 50 carbon atoms optionally containing one or more heteroatoms, subscript a is 0 to 2 and, optionally, when subscript a is 0 or 1, two $R^5$ groups may be bonded, together through a covalent bond to form a cyclized, alkoxysilyl group, or a polymer moiety derived from a resin for which flame retardant capability is desired, G having a valence equal to subscript n; subscript m is from 0 to about 50, more specifically from 0 to about 20 and still more specifically from 0 to about 8, provided, where subscript m is 0, $R^1$ is an oxygen atom and G contains at least one silicon atom which is bonded to the $R^1$ group; and, subscript n is from 1 to about 50, more specifically from 1 to about 10 and still more specifically from 1 to about 6.

In further accordance with the present invention, in triaryl silicon-containing compound (I), each Ar independently is an unsubstituted aryl group of from about 6 to about 20 carbon atoms or substituted aryl group of from about 6 to about 20 carbon atoms; each $R^2$ and $R^3$ independently is a monovalent hydrocarbon group of from 1 to about 8 carbon atoms; each $R^1$ is independently a divalent saturated or unsaturated hydrocarbon group of from 1 to about 45 carbon atoms, more specifically from 2 to about 30 carbon atoms, still more specifically from 2 to about 20 carbon atoms and most specifically from 2 to about 12 carbon atoms, optionally containing, one or more heteroatoms, specifically from 1 to about 20 oxygen, sulfur and/or nitrogen atoms, and still more specifically from 1 to about 10 oxygen atoms; and, G is selected from the group consisting of:

(a) a cyclic silicone of general formula (III):

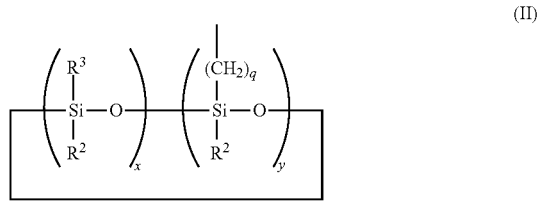

wherein:
each $R^2$ and $R^3$ independently is a monovalent hydrocarbon radical containing from to about 8 carbon atoms, more specifically from 1 to about 6 carbon atoms and still more specifically from 1 to 4 carbon atoms; subscript q is an integer of from 1 to about 6 and more specifically 1 or 2, subscript x is 0 to about 8, more specifically an integer of from 1 to about 6 and still more specifically from 1 to 3; and, subscript y is an integer of from 1 to about 8 more specifically from 1 to about 6 and still more specifically from 1 to 3, subject to the limitation that the value of subscript n=y;

(b) an acyclic silicone group of general formula (III):

wherein:
$M = R^4R^5R^6SiO_{1/2}$,
$M^* = R^4R^*R^6SiO_{1/2}$
$D = R^7R^8SiO_{2/2}$,
$D^* = R^7R^*SiO_{2/2}$
$T = R^9SiO_{3/2}$,
$T^* = R^*SiO_{3/2}$,
$Q = SiO_{4/2}$,
$A = O_{1/2}Si(R^{10})(R^{11})R^{12}Si(R^{13})(R^{14})O_{1/2}$
$B = O_{1/2}Si(R^{15})(R^{16})R^{17}Si(R^{18})O_{2/2}$
$C = O_{1/2}Si(R^{19})(R^{20})R^{21}SiO_{3/2}$
wherein:
$R^4, R^5, R^6, R^7, R^8, R^9, R^{10}, R^{11}, R^{13}, R^{14}, R^{15}, R^{16}, R^{18}, R^{19}$ and $R^{20}$ each independently is selected from the group consisting of $OR^{22}$ and monovalent hydrocarbon radical containing from 1 to about 20 carbon atoms, more specifically from 1 to about 12 carbon atoms and still more specifically from 1 to about 6 carbon atoms, optionally containing at least one of a heteroatom, e.g., O, N or S, an aromatic, group of from about 6 to about 10 carbon atoms, and a hydroxyl group; $R^{12}$, $R^{17}$ and $R^{21}$ each independently is a divalent hydrocarbon group of from 1 to about 8 carbon atoms and more specifically from 1 to about 4 carbon, atoms; $R^{22}$ is a monovalent hydrocarbon of from 1 to about 20 carbon atoms, more specifically from 1 to about 12 carbon atoms and still more specifically from 1 to about 6 carbon atoms; $R^*$ is a divalent hydrocarbon of from 1 to about 8 carbon atoms, more specifically from 1 to about 6 carbon atoms and still more specifically from 1 to 4 carbon atoms, where one of the valences of $R^*$ is bound to $R^1$; and, subscripts b, c, d, e, f, g, h, j and k are zero or positive subject to the limitation b+c+d+e+f+g+h+i+j<1000, more specifically <750, still more specifically 500 and most specifically 100, with the lower endpoints of any of said ranges of b+c+d+e+f+g+h+i+j being any one or more of 1, 2, 3, 5, 10, 12, 20, 50 or 60, provided, c+e+g≥1, more specifically c+e+g≥2, and still more specifically c+e+g≥3 with upper end points to such ranges of c+e+g being any one of 4, 5, 8, 10, 12, 20, 50, 60 or 100;

(c) an alkoxysilyl group $-R^*SiR^4_a(OR^5)_{3-a}$ wherein each, occurrence of $R^*$ is a divalent hydrocarbon of from 1 to about 8 carbon atoms, more specifically from 1 to about 6 carbon atoms and still more specifically from 1 to 4 carbon atoms, where one of the valences of $R^*$ is bonded to $R^1$ and each occurrence of $R^4$ is independently methyl, ethyl, propyl or isopropyl, each occurrence of $R^5$ independently is a monovalent hydrocarbon group of from 1 to about 50 carbon atoms, more specifically from 1 to about 12 carbon atoms, still more specifically from 1 to 4 carbon atoms and yet still more specifically 1 or 2 carbon atoms, optionally containing one or more heteroatoms, specifically from 1 to 20 oxygen atoms, sulfur atoms and/or nitrogen atoms; and a is 0 or 1, or cyclized alkoxysilyl group in which two $R^1$ groups are bonded together through a covalent bond, G having a valence equal to subscript n; subscript in is from 0 to about 50, more specifically from 0 to about 20 and still more specifically from 0 to about 8, provided, where subscript in is 0, $R^1$ is other than a chemical, bond and 0 contains at least one silicon atom; and, subscript n is from 1 to about 50, more specifically from 1 to about 10 and still more specifically from 1 to about 6; provided that when m is 0, each $R^1$ is independently a divalent saturated or unsaturated hydrocarbon group of from 1 to about 45 carbon atoms, more specifically from 2 to about 30 carbon atoms, still more specifically from 2 to about 20 carbon atoms and most, specifically from 2 to about 12 carbon atoms, optionally containing one or more heteroatoms, specifically from 1 to about 20 oxygen, sulfur and/or nitrogen atoms, and still more specifically from 1 to about 10 oxygen atoms; and, (d) a polymer moiety derived from a resin for which flame retardant capability is desired; and, subscript m being an integer of from 1 to about 50, more specifically from 2 to, about 20, still more specifically from 2 to about and most specifically 1, provided, where m is 1, G is polymer moiety (d).

In still further accordance with the present invention, in triaryl silicon-containing compound (I), each Ar independently is an unsubstituted aryl group of from about 6 to about 20 carbon atoms or a substituted aryl group of from about 6 to about 20 carbon atoms; each $R^2$ and $R^3$ independently is selected from a monovalent hydrocarbon group of from 1 to about 8 carbon atoms; each $R^1$ is independently a divalent saturated or unsaturated hydrocarbon group of from 1 to about 45 carbon atoms optionally containing one or more heteroatoms or a chemical bond; G is a hydroxyl group, a triarylsilyloxy group, an alkoxysilyl group of general formula $-SiR^4_a(OR^5)_{3-a}$ wherein each occurrence of $R^4$ and $R^5$ independently is a monovalent hydrocarbon group of from 1 to about 12 carbon atoms and subscript a is 0 to 2, or where subscript a is 0 or 1 a cyclized alkoxysilyl group obtained therefrom, or a polymer moiety, G having a valence equal to subscript n and each of subscripts m and n independently being from 1 to about 50.

In yet still further accordance with the present invention, in triaryl silicon-containing compound (I), each Ar independently is an unsubstituted aryl group of from about 6 to about 20 carbon atoms or a substituted aryl group of from about 6 to about 20 carbon atoms; each $R^2$ and $R^3$ independently is selected from a monovalent hydrocarbon group of from 1 to about 8 carbon atoms; each $R^1$ is a chemical bond; G is a triarylsilyloxy group having a valence of 1; and, each occurrence of subscript in independently is from 0 to about 50.

Without intending to be bound, at an early stage of combustion of the flame-retarded resin herein, silyl radicals are thought to form after releasing, aryl groups from the triaryl silicon-containing (I) flame retardant additive. These silyl radicals then become available to crosslink the host resin/resin blend. During combustion, triaryl silicon-containing compound (I) may also form a char barrier at the surface of the resin that acts to reduce the radiant heat of the flame as well as to reduce the diffusion of combustion products into the combustion zone, both effects serving to retard flame propagation.

A number of triaryl silicon-containing compounds (I) and their preparation are known from U.S. Pat. No. 9,422,315, the entire contents of which are incorporated by reference herein. These compounds are disclosed in U.S. Pat. No. 9,422,315 as additives for personal care compositions to which their high refractive indices impart improved luster and shine. Nothing is said in U.S. Pat. No. 9,422,315 of the triaryl silicones disclosed therein as useful as flame retardant additives for flame-retarded resins.

Further in accordance with the present invention, there is provided a novel triaryl silicon-containing compound of general formula (Ia):

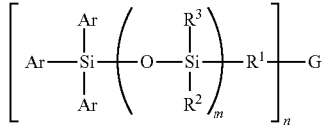

(Ia)

wherein each Ar independently is an unsubstituted aryl group of from about 6 to about 20 carbon atoms or a substituted aryl group of from about 6 to about 20 carbon atoms; $R^2$ and $R^3$ each independently is selected from a monovalent hydrocarbon group of from 1 to about 8 carbon atoms; each $R^1$ is independently a divalent saturated or unsaturated hydrocarbon group of from 1 to about 45 carbon atoms, optionally containing one or more heteroatoms, or a chemical bond; G is an organic group having a valence equal to subscript n, the subscript a is 0 to 2, and each of subscripts m and n independently being from 1 to about 50, with the provisos that (i) when m is equal to 1 and R is a divalent saturated or unsaturated hydrocarbon group of from 1 to about 45 carbon atoms, then G is an alkoxysilyl group —$SiR^4_a(OR^5)_{3-a}$, wherein each occurrence of $R^4$ is independently a monovalent hydrocarbon group of from 1 to about 12 carbon atoms; each occurrence of $R^5$ independently is a monovalent hydrocarbon of from 1 to about 50 carbon atoms, an organic group derived from a resin having more than about 30 carbon atoms and selected from the group consisting of polycarbonates, polyacetals, polyesters, polysulfones, polyamides, polyimides, polyetherimides, polyetherether ketones, polystyrenes, polyurethanes, polyisocyanurates, polyepoxides, phenol formaldehyde resins, polyphenylene oxides, polyphenylene sulfides, polylactides, polyolefins, styrene-ethylene-butylene-butylenes (STEBS) copolymer, acrylics, acrylonitrile butadiene styrene (ABS) terpolymers, styrene acrylonitrile (SAN) rubbers, acetals, polyimidazoles, polytetrafluoroethylene (TPFE), polyvinyl chloride (PVC) and polyvinylidene chloride, where a carbon atom of the $R^5$ group is bonded to the oxygen atom of the —$OR^5$ group, or a cyclized alkoxysilyl group in which two $R^5$ groups, when present, are bonded together through a covalent bond, and (ii) when m is 2 to about 50, then G is selected from the group consisting of:
(a) a linear or branched acyclic organic group having up to about 45 carbon atom or a cyclic organic group of from 3 to about 20 carbon atoms either of which is a saturated or unsaturated hydrocarbon radical optionally containing at least one of a heteroatom, carbonyl group, ester group, amide group or hydroxyl group, and having a valence of from 1 to about 25, more specifically from 1 to about 15 and still more specifically from 1 to about 6, subject to the requirement that the valence of the organic group is equal to the value of subscript n;
(b) a cyclic silicone of general formula (II):

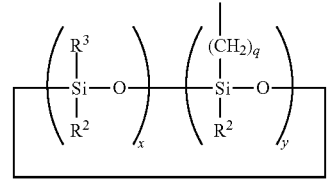

(II)

wherein:
each $R^2$ and $R^3$ independently is a monovalent hydrocarbon radical containing from 1 to about 8 carbon atoms, more specifically from 1 to about 6 carbon atoms and still more specifically from 1 to 4 carbon atoms; subscript q is an integer of from 1 to about 6 and more specifically 2 or 3, subscript x is 0 to about 8, more specifically from 1 to about 6 and still more specifically from 1 to 3, and subscript y is an integer of from 1 to about 8, more specifically from 1 to about 6 and still more specifically from 1 to 3, subject to the requirement that the value of subscript n=y;
(c) an acyclic silicone group of general formula (III):

$$M_b M^*_c D_d D^*_e T_f T^*_g Q_h A_i B_j C_k \quad \text{(III)}$$

wherein:
$M = R^4 R^5 R^6 SiO_{1/2}$,
$M^* = R^4 * R^6 SiO_{1/2}$
$D = R^7 R^8 SiO_{2/2}$,
$D^* = R^7 R^* SiO_{2/2}$
$T = R^9 SiO_{3/2}$,
$T^* = R^* SiO_{3/2}$,
$Q = SiO_{4/2}$,
$A = O_{1/2} Si(R^{10})(R^{11})R^{12} Si(R^{13})(R^{14})O_{1/2}$
$B = O_{1/2} Si(R^{15})(R^{16})R^{17} Si(R^{18})O_{2/2}$
$C = O_{1/2} Si(R^{19})(R^{20})R^{21} SiO_{3/2}$
wherein:
$R^4$, $R^5$, $R^6$, $R^7$, $R^8$, $R^9$, $R^{10}$, $R^{11}$, $R^{13}$, $R^{14}$, $R^{15}$, $R^{16}$, $R^{18}$, $R^{19}$ and $R^{20}$ each independently is selected from the group consisting of OR and monovalent hydrocarbon radical containing from 1 to about 20 carbon atoms, more specifically from 1 to about 12 carbon atoms and still more specifically from 1 to about 6 carbon atoms, optionally containing at least one of a heteroatom, e.g., O, N or S, an aromatic group of from 6 to 10 carbon atoms, and a hydroxyl group; $R^{12}$, $R^{17}$ and $R^{21}$ each independently is a divalent hydrocarbon group of from 1 to about 8 carbon atoms and more specifically from 1 to 4 carbon atoms; $R^{22}$ is a monovalent hydrocarbon group of from 1 to about 20 carbon atoms, more specifically from 1 to about 12 carbon atoms and still more specifically from 1 to about 6 carbon atoms; R* is a divalent hydrocarbon of from 1 to about 8 carbon atoms, more specifically from 1 to about 6 carbon atoms and still more specifically from 1 to 4 carbon atoms where one of the valences of R* is bound to $R^1$; and, subscripts b, c, d, e, f, g, h, i, j and k are zero or positive subject to the requirement that b+c+d+e+f+g+h+i+j+k<1000, more specifically 750, still more specifically <500 and most specifically <100, with the lower endpoints of any of said ranges of b+c+d+e+f+g+h+i+j+k being any one or more of 1, 2, 3, 5, 10, 12, 20, 50 or 60, provided, c+e+g≥1, more specifically c+e+g≥2, and still more specifically c+e+g≥3 with upper end points of such ranges of c+e+g being any one of 4, 5, 8, 10, 12, 20, 50, 60 or 100;

(d) an alkoxysilyl group —$R*SiR^4_a(OR^5)_{3-a}$, wherein R* is a divalent hydrocarbon of from 1 to about 8 carbon atoms, more specifically from 1 to about 6 carbon atoms and still more specifically from 1 to 4 carbon atoms, one of the valences of R* being bonded to $R^1$, each occurrence of $R^4$ independently is a monovalent hydrocarbon group of from 1 to about 12 carbon atoms, more specifically methyl, ethyl, propyl or isopropyl; each occurrence of $R^5$ independently is a monovalent hydrocarbon of from 1 to about 50 carbon atoms, more specifically from 1 to 12 carbon atoms, still more specifically from 1 to 4 carbon atoms, and yet more, specifically, from 1 to 2 carbon atoms, an organic group derived from a resin having more than 30 carbon atoms and selected from the group consisting of polycarbonates, polyacetals, polyesters, polysulfones, polyamides, polyimides, polyetherimides, polyetherether ketones, polystyrenes, polyurethanes, polyisocyanurates, polyepoxides, phenol formaldehyde resins, polyphenylene oxides, polyphenylene sulfides, polylactides, polyolefins, styrene-ethylene-butylene-butylenes (STEBS) copolymer, acrylics, acrylonitrile butadiene styrene (ABS) terpolymers, styrene acrylonitrile (SAN) rubbers, acetals, polyimidazoles, polytetrafluoroethylene (TPFE), polyvinyl chloride (PVC) and polyvinylidene chloride, and more specifically polycarbonate, where a carbon atom of the $R^5$ group is bonded to the oxygen atom of the —$OR^5$ group, or a cyclized alkoxysilyl group in which two $R^5$ groups, when present, are bonded together through a covalent bond; and, (e) a polymer moiety derived from a resin for which flame retardant capability is desired.

DETAILED DESCRIPTION OF THE INVENTION

The expression "flame retardant resin composition" shall be understood herein to mean at least one extruded, molded, cast and/or calendered thermoplastic, thermosetting or elastomeric resin which does not contain a triarylsilyloxy group, and for which flame retardant capability is desired, such resin or resin mixture containing at least one flame retardant additive in physical admixture therewith and/or chemically bonded thereto.

The terms "polymer" and "resin" are used interchangeably herein and refer to such materials that are macromolecules formed by the chemical union of five or more identical combining units, which are monomers and in the bulk form are solid, in contrast to liquid or flowable, at ambient temperatures.

The expressions "chemically incorporated" and "chemically bonded" as they apply to the relationship of the flame retardant compound to its host resin contemplates any such relationship in which the flame retardant compound is attached to the structure of the host resin and not merely in physical admixture therewith.

Other than in the working examples, or where otherwise indicated, all numbers expressing amounts of materials, reaction conditions, time durations, quantified properties of materials, and so forth, stated in the specification and claims are to be understood as being, modified in all instances by the term "about".

It will be understood that any numerical range recited herein includes all sub-ranges within that range and any combination of the various endpoints of such ranges or sub-ranges whether described in the examples or anywhere else in the specification.

It will also be understood herein that any of the components of the invention herein as they are described by any specific genus or species detailed in the examples section of the specification, can be used in one embodiment to define an alternative respective definition of any endpoint of a range elsewhere described in the specification with regard to that component, and can thus, in one non-limiting embodiment, be used to supplant such a range endpoint, elsewhere described.

It will be farther understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting, materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the instant invention as a reaction product of initial materials reference is made to the initial species recited and it is to be noted that additional materials may be, added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example particulate solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

As used herein the term "alkyl" means a saturated straight or branched monovalent hydrocarbon group. In a preferred embodiment, monovalent alkyl groups are selected from linear or branched alkyl groups of from 1 to 6 carbons atoms per group, such as, for example, methyl, ethyl, propyl, iso-propyl, n-butyl, iso-butyl, see-butyl, tert-butyl, pentyl, iso-pentyl, neopentyl, tert-pentyl, 2,2,4-trimethylpentyl, hexyl and so forth.

As used herein, the term "cycloalkyl" means a saturated cyclic monovalent hydrocarbon group. In a preferred embodiment, monovalent cycloalkyl groups are selected from cycloalkyl groups having from about 5 to about 10 carbon atoms per group such as, for example, cyclopentyl, cyclohexyl, cyclodecyl and so forth.

As used herein the term "alkenyl" means a straight or branched monovalent ethylenically unsaturated hydrocarbon group, specifically containing from 2 to 4 carbon atoms per radical, such as, for example, vinyl, allyl, 2-propenyl and 3-butenyl.

The expressions "divalent alkyl", "divalent alkenyl", "divalent alkynyl" and "divalent aryl" refer to the specified hydrocarbon compounds from which two hydrogen atoms have been removed.

As used herein, "Ar" means an aryl group and includes, for example, phenyl, tolyl, xylyl, naphthyl, naphthalenyl, anthracenyl, phenanthyl, and the like.

A. Resin for Which Flame Retardant Capability is Desired

Any resin, which does not contain a triarylsilyloxy group, for which flame retardant capability is desired ("host resin"), e.g., any of the thermoplastic, thermosetting and elastomeric (inclusive of rubber) resins and blends of such resins to which flame retardant capability is to be imparted.

Host resins to which triaryl silicon-containing compound (I) may be added or combined as a flame retardant include, without limitation, polycarbonates, polyacetals, polyesters, polysulfones, polyamides, polyimides, polyetherimides, polyetherether ketones, polystyrenes, polyurethanes, polyisocyanurates, polyepoxides, phenol formaldehyde resins, polyphenylene oxides, polyphenylene sulfides, polylactides, polyolefins such as polyethylene, polypropylene, thermoplastic elastomers such as, but not limited to, styrene-ethylene-butylene-butylenes (STEBS) copolymer, acrylics, acrylonitrile butadiene styrene (ABS) terpolymers, styrene acrylonitrile (SAN) rubbers, acetals, polyimidazoles, polytetrafluoroethylene (TPFE), polyvinyl chloride (PVC), polyvinylidene chloride, and the like, as well as mixtures, e.g., blends, thereof. It is particularly advantageous to incorporate triaryl silicon-containing compound (I) as a flame retardant in a polycarbonate or polycarbonate-containing resin blend.

Triaryl silicon-containing compound (I) may be incorporated in the selected host resin employing any conventional or otherwise known technique. Where compatibility of resin and triaryl silicon-containing compound (I) may be an issue, a compatibilizer may be included its the composition in accordance with known and conventional practice. Where the thermoplastic resin is of the aromatic type, the use of a compatibilizer may ordinarily be dispensed with due to the typically compatible nature of such resin and triaryl silicon-containing compound (I).

B. Flame Retardant Resin Composition

The flame retardant resin composition herein comprises at least one resin which does not contain a triarylsilyloxy functional group and for which flame retardant capability is desired, e.g., as listed above, and at least one triaryl silicon-containing compound (I) in admixture therewith. The at least one triaryl silicon-containing compound (I) during the process of being incorporated or combined with its host resin may undergo a chemical reaction with the resin to form a different triaryl silicon-containing compound (I) that is chemically bonded to the resin thereby forming a triaryl silicon-containing compound (I) derived from the resin.

In one non-limiting embodiment, in triaryl silicon-containing compound (I), each Ar is phenyl.

In another non-limiting embodiment, each $R^1$ in the triaryl silicon-containing compound (I) independently is a divalent alkyl, alkenyl, alkynyl or aryl group of up to about 45 carbon atoms, more specifically up to about 30 carbon atoms and still more specifically up to about 12 carbon atoms, optionally containing from 1 to about 20 oxygen, sulfur and/or nitrogen, atoms and more specifically from 1 to about 10 oxygen atoms.

In another non-limiting embodiment, G is a silicon-containing group, more specifically a triarylsilyl ($Ar_3Si$—) group and still more specifically a triphenylsilyl ($Ph_3Si$—) group, with subscript in as previously defined and subscript n equal to 1.

In yet another non-limiting embodiment, G is a hydrogen atom, an acyclic organic group of from 1 to about 8 carbon atoms, more specifically from 2 to about 8 carbon atoms and still more most specifically from 4 to about 6 carbon atoms, an alkoxysilyl group of the general structure —$SiR^4_a(OR^5)_{3-a}$ wherein each occurrence of $R^4$ and $R^5$ independently is methyl, ethyl, propyl or isopropyl and subscript a is 0 or 1, subscript in is an integer of from 1 to about 8 and subscript n is an integer of from 1 to about 8.

In still another non-limiting embodiment, triaryl silicon-containing compound (I) is such as described herein with G being selected from the group consisting of:

(a) a linear or branched acyclic organic group having up to about 45 carbon atom or a cyclic organic group of from 3 to about 20 carbon atoms either of which is a saturated or unsaturated hydrocarbon radical and optionally containing at least one of a heteroatom, carbonyl group, ester group, amide group or hydroxyl group, and having a valence of from 1 to about 25, more specifically from 1 to about 15 and still more specifically from 1 to about 6, subject to the requirement that the valence of the organic group is equal to the value of subscript n;

(b) a cyclic silicone of general formula (II):

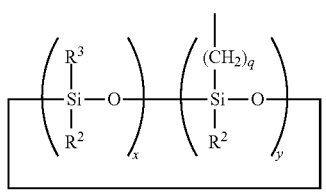

wherein:
each $R^2$ and $R^3$ independently is a monovalent hydrocarbon radical containing from 1 to about 8 carbon atoms, more specifically from 1 to about 6 carbon atoms and still more specifically from 1 to 4 carbon atoms; subscript q is an integer of from 1 to about 6 and more specifically 2 or 3, subscript x is 0 to about 8, more specifically from 1 to about 6 and still more specifically from 1 to 3, and subscript is an integer of from 1 to about 8, more specifically from 1 to about 6 and still more specifically from 1 to 3, subject to the requirement that the value of subscript n=y;

(c) an acyclic silicone group of general formula (III):

$$M_b M^*_c D_d D^*_e T_f T^*_g Q_h A_i B_j C_k \quad (III)$$

wherein:
$M = R^4 R^5 R^6 SiO_{1/2}$,
$M^* = R^4 R^* R^6 SiO_{1/2}$
$D = R^7 R^8 SiO_{2/2}$,
$D^* = R^7 R^* SiO_{2/2}$
$T = R^9 SiO_{3/2}$,
$T^* = R^* SiO_{3/2}$,
$Q = SiO_{4/2}$,
$A = O_{1/2} Si(R^{10})(R^{11})R^{12}Si(R^{13})(R^{14})O_{1/2}$
$B = O_{1/2} Si(R^{15})(R^{16})R^{17}Si(R^{18})O_{2/2}$
$C = O_{1/2} Si(R^{19})(R^{20})R^{21}SiO_{3/2}$
wherein:
$R^4, R^5, R^6, R^7, R^8, R^9, R^{10}, R^{11}, R^{13}, R^{14}, R^{15}, R^{16}, R^{18}, R^{19}$ and $R^{20}$ each independently is selected from the group consisting of $OR^{22}$ and monovalent hydrocarbon radical containing from 1 to about 20 carbon atoms, more specifically from 1 to about 12 carbon atoms and still more specifically from 1 to about 6 carbon atoms, optionally containing at least one of a heteroatom, e.g., O, N or S, an aromatic group of from 6 to 10 carbon atoms, and a hydroxyl group; $R^{12}$, $R^{17}$ and $R^{21}$ each independently is a divalent hydrocarbon group of from 1 to about 8 carbon atoms and, more specifically from 1 to 4 carbon atoms; $R^{22}$ is a monovalent hydrocarbon group of from 1 to about 20 carbon atoms, more specifically from 1 to about 12 carbon atoms and still more specifically from 1 to about 6 carbon atoms; $R^*$ is a divalent hydrocarbon of from 1 to about 8 carbon atoms, more specifically from 1 to about 6 carbon atoms and still, more specifically from 1 to 4 carbon atoms where one of the valences of $R^*$ is bound to $R^1$; and, subscripts b, c, d, e, f, g, h, i, j and k are zero or positive subject to the requirement that b+c+d e+f+g+k<1000, more specifically <750, still more specifically <500 and most specifically <100, with the lower endpoints of any of said ranges b+c+d+e+f+g+h+i+j+k being any one or more of 1, 2, 3, 5, 10, 12, 20, 50 or 60, provided, c+e+g≥1, more specifically c+e+g≥2, and still more specifically c+e+g≥3 with upper end points of such ranges of c+e+g being any one of 4, 5, 8, 10, 12, 20, 50, 60 or 100;

(d) an alkoxysilyl group $—SiR^4_a(OR^5)_{3-a}$ wherein each occurrence of $R^4$ and $R^5$ is independently methyl, ethyl, propyl or isopropyl and a is 0 or 1, or cyclized alkoxysilyl group in which two $R^5$ groups are bonded together through a covalent bond; and, (e) a polymer moiety derived from a resin for which flame retardant capability is desired.

In one non-limiting embodiment of general formula (I), each $R^1$ is independently a divalent alkyl group of from 2 to about 6 carbon atoms, more specifically from 2 to 4 carbon atoms and still more specifically 2 or 3 carbon atoms such as the non-limiting examples of ethylene, propylene and isopropylene.

In one non-limiting embodiment of general formula (I), each $R^1$ is a divalent unsaturated hydrocarbon group of, for example, 2 to 4 carbon atoms such as vinyl, and G is a hydrogen atom terminating the $R^1$ group. In another non-limiting embodiment, $R^1$ is a divalent saturated hydrocarbon group containing from 1 to about 6 carbon atoms, more specifically from 1 to 4 carbon atoms and still more specifically from 1 to 3 carbon atoms, and G is a hydrogen atom terminating the $R^1$ group.

In another non-limiting embodiment of general formula (I), $R^1$ is $—CH_2CH_2—$ and G is $—SiR^4_a(OR^5)_{3-a}$, wherein each occurrence of $R^4$ and $R^5$ independently is methyl, ethyl, propyl or isopropyl, preferably ethyl, and a is 0 or 1.

In another non-limiting embodiment of formula (I), the silicon-containing group in the definition of G in formula (I) is a silicone-containing group of from 2 to about 20 silicon atoms, more specifically from 2 to 18 silicon atoms, still more specifically from 2 to about 12 silicon atoms and most specifically from 2 to about 8 silicon, atoms, for example, in certain non-limiting embodiments 2, 3 or 4 silicon atoms.

In another non-limiting embodiment of triaryl silicon-containing compound (I), each Ar is phenyl, triphenyl silicon-containing compound of the general formula (Ib):

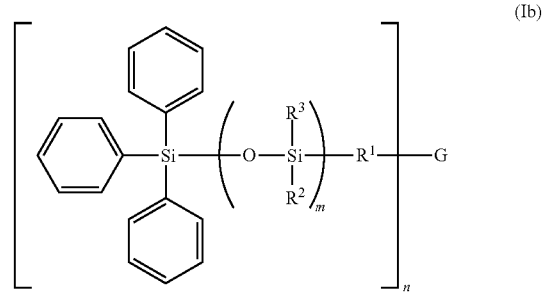

wherein groups $R^1$, $R^2$, $R^3$, and C and integers m and n are as previously defined.

In another non-limiting embodiment herein, triphenyl silicon-containing compound (I) is of general formula (Ic):

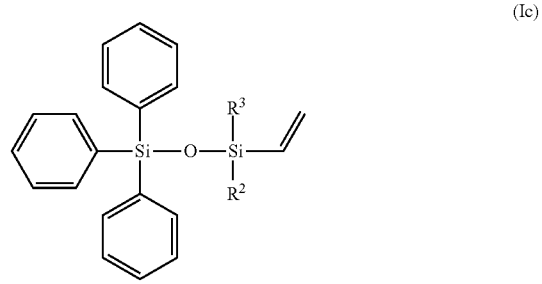

wherein each $R^2$ and $R^3$ independently is as previously defined, and more specifically, each $R^2$ and $R^3$ independently is an alkyl group of from 1 to 3 carbon atoms.

Triphenyl silicone (Ic) can be grafted onto a suitable resin, e.g., a polyolefin, employing a free radical catalyst in accordance with procedures that are themselves well known in the art, in this manner imparting flame retardant capability to the resin. In one particular non-limiting embodiment of such grafting procedure triphenyl silicon-containing compound (Ib) in which each of $R^2$ and $R^3$ is methyl, i.e., the triphenyl-dimethyl-3,3,3-triphenyl-1-vinyldisiloxane, is grafted onto polyethylene as shown below:

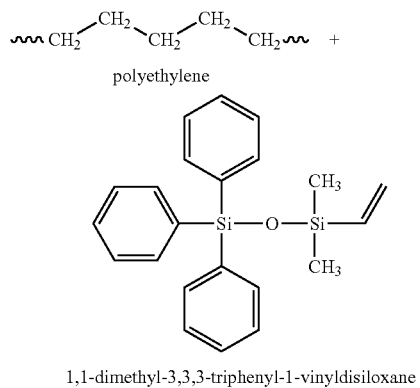

polyethylene

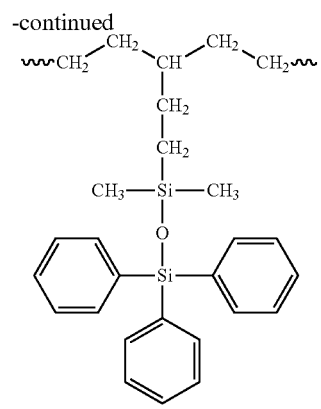

1,1-dimethyl-3,3,3-triphenyl-1-vinyldisiloxane triphenyl dimethylsilcione grafted polyethylene In other embodiments herein, in triphenyl silicon-containing compound (Ib), when G is an acyclic silicone group of general formula (III), supra, subscripts b, c, d, e, f and g are as previously defined and the sum of subscripts i+j+k is ≥1, more specifically ≥2 and still more specifically ≥3 with upper endpoints such as 5, 6, 8, 10, 12, 15, 20, 50, or the like.

Some specific embodiments of triphenyl silicon-containing compound (Ia) are individual compounds or mixtures of compounds having structures selected from the group consisting of:

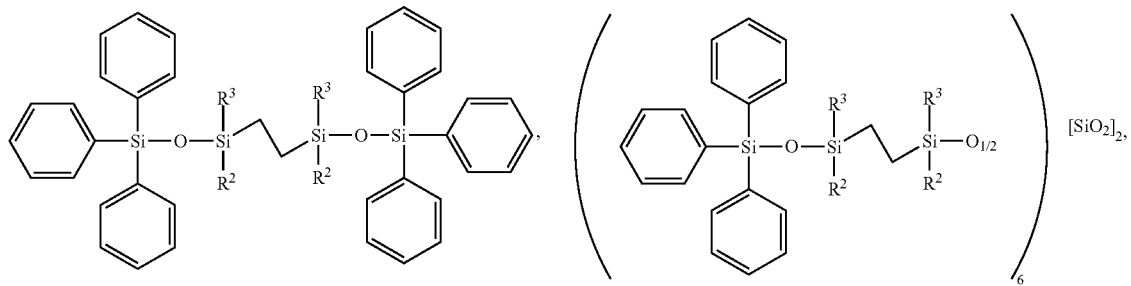

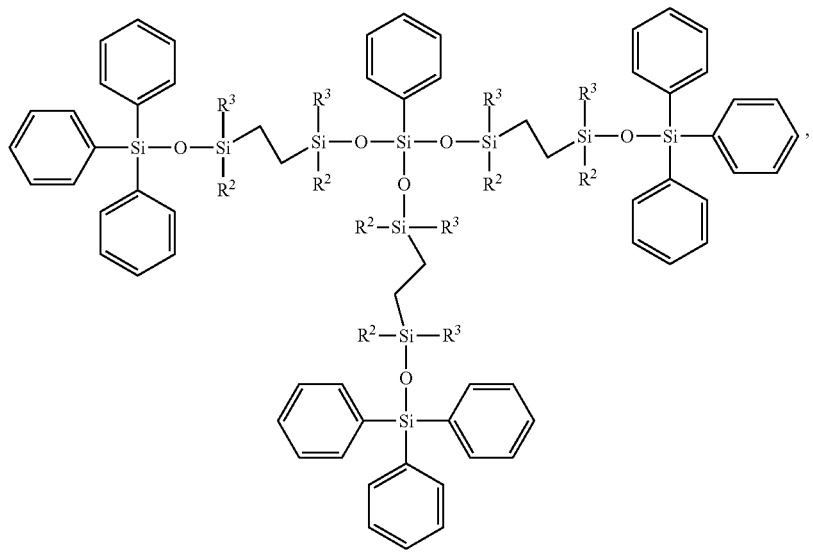

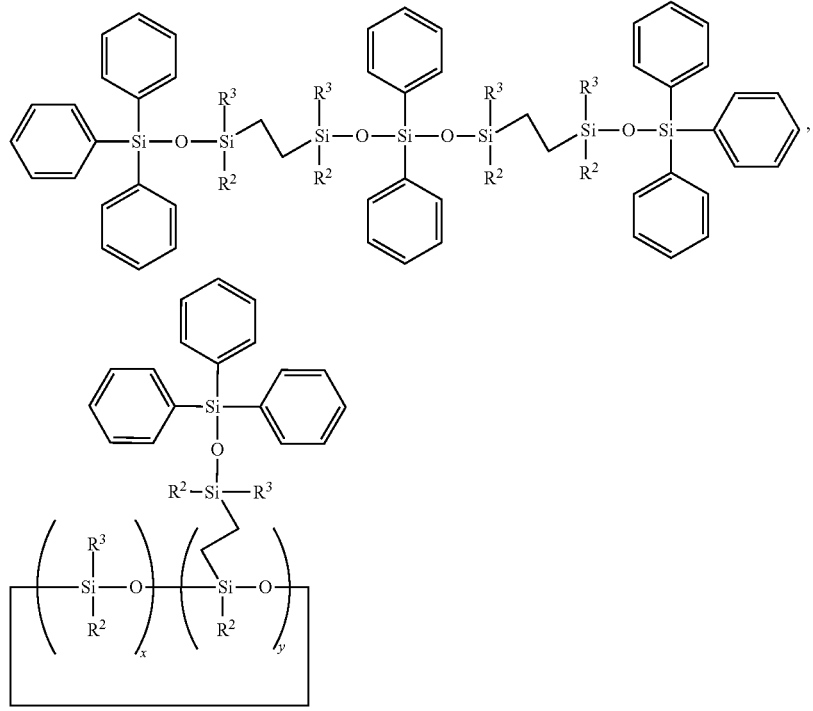
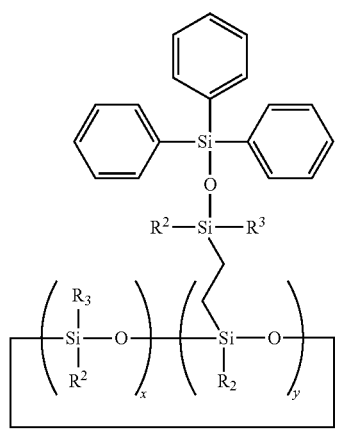
wherein x is 2 and y is 2,
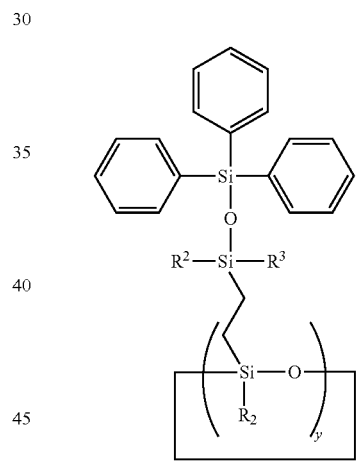
wherein y is 4,
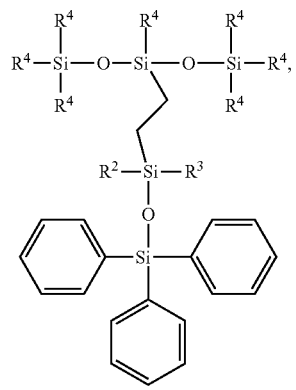
wherein x is 1 and y is 3,

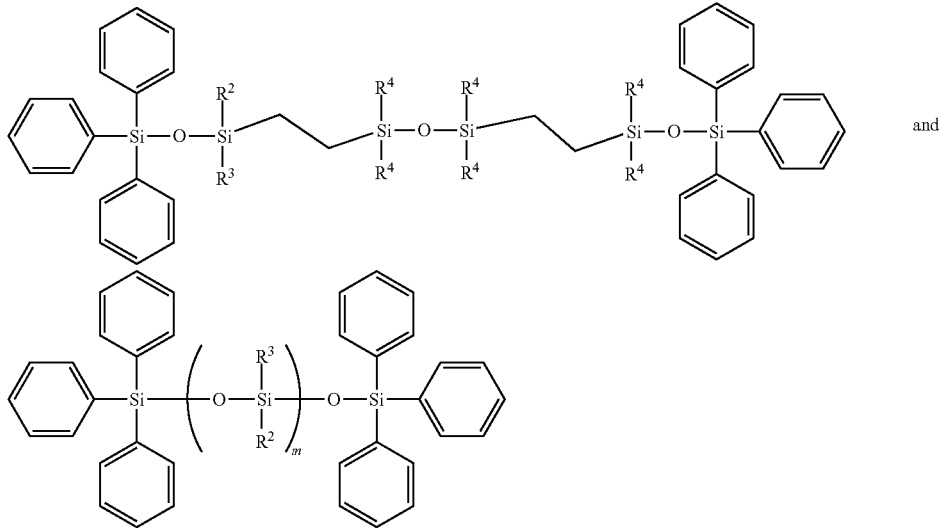 and wherein $R^2$, $R^3$ and $R^4$ each independently is a monovalent hydrocarbon group of from 1 to about 6 carbon atoms.

In one non-limiting embodiment of the foregoing structural formulas subscript m is an integer of from 1 to about 8, more specifically from 2 to about 8 and still more specifically from 1 to 4.

In another non-limiting embodiment of the foregoing formulas, each of $R^2$ and $R^3$ is methyl.

In yet another non-limiting embodiment herein, triphenyl silicon-containing compound (Ia) is of the formula:

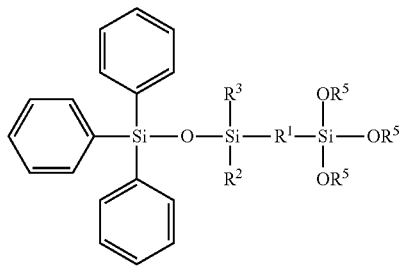

wherein $R^1$, $R^2$, $R^3$ and $R^5$ are as previously defined. In one particular non-limiting embodiment of the foregoing triphenyl silicon-containing compound (Ia), $R^2$ and $R^3$ each is methyl, $R^1$ is —CH$_2$CH$_2$— and each $R^5$ is ethyl, i.e., the compound 1,1-dimethyl-3,3,3-triphenyl-1-(2-triethoxysilanyl-ethyl)-disiloxane (TPTES-1), when $R^1$ is —CH(CH$_3$)—, the compound is 1,1-dimethyl-3,3,3-triphenyl-1-(1-triethoxysilanyl-ethyl)-disiloxane (TPTES-2):

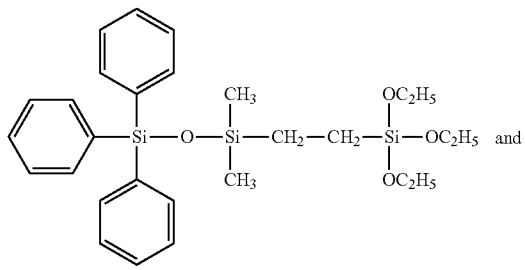 and

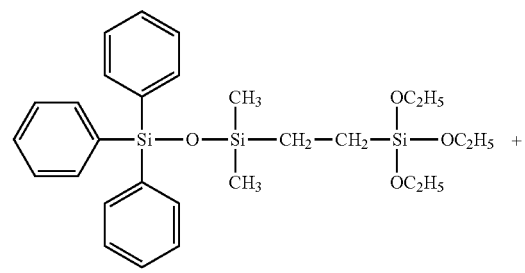

TPTES can be reacted with a diol, for example, 2-methylpentane 1,3-diol, to produce the cyclized derivative 2-[2-(1,1-dimethyl-3,3,3-triphenyl-disiloxanyl)-ethyl]-2-ethoxy-4-ethyl-5-methyl-[1,3,2]dioxasilinane (TPMES) as shown below:

TPTES-1

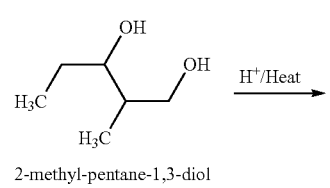

2-methyl-pentane-1,3-diol

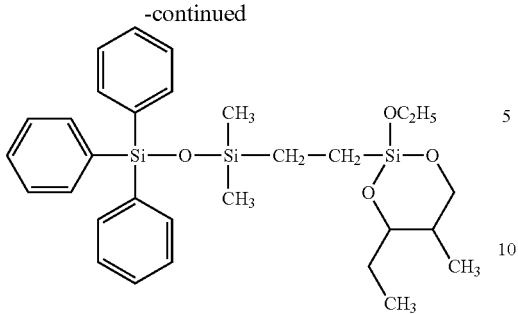

TPMES-1

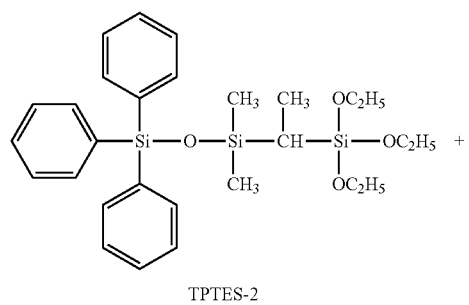

TPTES-2

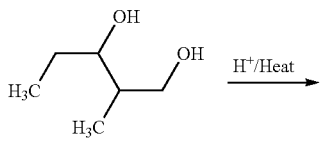

2-methyl-pentane-1,3-diol

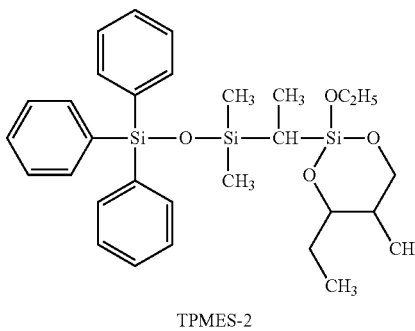

TPMES-2

TPTES and TPMES are both suitable for blending with a polymer and condensation catalyst (e.g., a tin salt including dibutyl tin dilaurate, dioctyltin dilaurate, an acid, a base, etc.) and subsequently crosslinked after hydrolysis of alkoxy groups in the presence of such catalyst and moisture followed by condensation polymerization of the resulting hydrolyzed products. This crosslinking will offer restricted flow of the resulting polymer blend, enhanced flame retardancy, better thermal stability and improved mechanical properties.

In one embodiment, the flame retardant resin composition comprises:

(a) at least one resin which does not contain a triarylsilyloxy group;

(b) at least one triaryl silicon-containing compound of general formula (I):

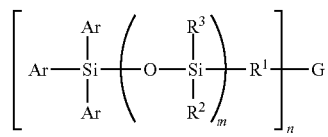

wherein each Ar independently is an unsubstituted aryl group of from about 6 to about 20 carbon atoms or substituted aryl group of from about 6 to about 20 carbon atoms; each $R^2$ and $R^3$ independently is a monovalent hydrocarbon group of from 1 to about 8 carbon atoms; each $R^1$ independently is a divalent saturated or unsaturated hydrocarbon group of from 1 to about 45 carbon atoms optionally containing one or more heteroatoms; G is an alkoxysilyl group —$SiR^4_a$ $(OR)_{3-a}$, wherein each occurrence of $R^4$ is independently a monovalent hydrocarbon group of from 1 to about 12 carbon atoms each occurrence of $R^5$ independently is a monovalent hydrocarbon of from 1 to about 50 carbon atoms, an organic group derived from a resin having more than 30 carbon atoms and selected from the group consisting of polycarbonates, polyacetals, polyesters, polysulfones, polyamides, polyimides, polyetherimides, polyetherether ketones, polystyrenes, polyurethanes, polyisocyanurates, polyepoxides, phenol formaldehyde resins, polyphenylene oxides, polyphenylene sulfides, polylactides, polyolefins, styrene-ethylene-butylene-butylenes (STEBS) copolymer, acrylics, acrylonitrile butadiene styrene (ABS) terpolymers, styrene acrylonitrile (SAN) rubbers, acetals, polyimidazoles, polytetrafluoroethylene (TPFE), polyvinyl chloride (PVC) and polyvinylidene chloride, where a carbon atom of the $R^5$ group is bonded to the oxygen atom of the —$OR^5$ group, or a cyclized alkoxysilyl group in which two $R^5$ groups, when present, are bonded together through a covalent bond, subscript m is from 1 to about 50 and the subscript n is 1; and, (c) at least one condensation catalyst, e.g., dibutyl tin dilaurate, dioctyltin dilaurate, acid, base, etc.

Many of the triaryl silicon-containing compounds of formula (I) can be prepared in accordance with processes described in U.S. Pat. No. 9,422,315, the contents of which are incorporated by reference herein in their entirety, and modifications thereof as will be apparent to those skilled in the art. Other triaryl silicon-containing compounds of formula (I) can be prepared in accordance with, processes hereinafter described and modifications thereof as will also be apparent to those skilled in the art.

Synthesis of triphenyl dimethyl silicone-containing compounds (I) can be carried out by hydrosilylation of a linear or cyclic silicon-containing hydride with an, allyl or vinyl functional triphenyl silicon-containing compound or by the hydrosilylation of a silyl hydride functional triphenyl silicon-containing compound (I) with an ally or vinyl functional hydrocarbon. The hydrosilylation can be carried out in the presence of a hydrosilation catalyst based on noble metals such as but not limited to platinum, ruthenium, palladium or rhodium based catalyst. The reaction can be achieved with or without an organic solvent.

Specific embodiments of synthetic procedures for preparing triaryl silicon-containing compound of formula (I) are as follows:

Hydrosilylation of Linear Silicon-Containing Hydride with 1,1,1-Triphenyl-3,3-Dimethyl-3-Vinyl Disiloxane A linear silicon-containing hydride and 1,1,1-triphenyl-3,3-dimethyl-3-vinyl disiloxane are reacted in the presence of a hydrosilylation catalyst. Art aprotic solvent such as toluene may optionally be used. The temperature of the reaction mixture is from room temperature to about 120° C., more specifically from about 40° to about 90° C. The reaction is exothermic and is accompanied by a rise in temperature. Depending on the reaction temperature, the reaction time can vary from about 1 to about 48 hours, more specifically from about 3 to about 8 hours, the reaction being considered complete upon disappearance from the infrared spectrum of the reaction mixture of the Si—H peak. When an aprotic solvent is used, the solvent may be removed by stripping or distillation optionally under reduced pressure (vacuum) to provide a substantially solvent-free product.

Hydrosilylation of Cyclic Silicon-Containing Hydride with 1,1,1-Triphenyl-3,3-Dimethyl-3-Vinyl Disiloxane A cyclic silicon-containing hydride and 1,1,1-triphenyl-3,3-dimethyl-3-vinyl disiloxane are reacted in the presence of a hydrosilylation catalyst. An aprotic solvent such as toluene may optionally be used. The temperature of the reaction mixture is from room temperature to about 120° C., more specifically from about 40° to about 90° C., The reaction is exothermic and produces a sudden rise in temperature. The reaction time is from 1 to about 48 hours, more specifically from 3 to 8 hours, the reaction being considered complete upon the disappearance from the infrared spectrum of the reaction mixture of the Si—H peak. When an aprotic solvent, is used, the solvent may be removed by stripping or distillation optionally under reduced pressure (vacuum) to provide a substantially solvent-free product.

Hydrosilylation of Linear Silicon-Containing Hydride with 1,1,1-Triphenyl-3,3-Dimethyl-3-Allyl Disiloxane A linear silicon-containing hydride and 1,1,1-triphenyl-3,3-dimethyl-3-allyl disiloxane are reacted in the presence of a hydrosilylation catalyst. An aprotic solvent such as toluene may optionally be used. The temperature of the reaction mixture is from room temperature to about 120° C., more specifically from about 40° to about 90° C. The reaction is exothermic and results in a sudden rise in temperature. The reaction time is from 1 to about 48 hours, more specifically from 3 to 8 hours, the reaction being considered complete with the disappearance of the peak from the infrared spectrum of the reaction mixture. When an aprotic solvent is used, the solvent may be removed by stripping or distillation optionally under reduced pressure (vacuum) to provide a substantially solvent-free product.

Hydrosilylation of Cyclic Silicon-Containing Hydride with 1,1,1-Triphenyl-3,3-Dimethyl-3-Allyl Disiloxane A cyclic silicon-contain log hydride and 1,1,1-triphenyl-3,3-dimethyl-3-allyl disiloxane are reacted in the presence of a hydrosilylation catalyst. An aprotic solvent such as toluene may optionally be used. The temperature of the reaction mixture is from room temperature to about 120° C., more specifically from about 40° to about 90° C. The reaction is exothermic and results in a sudden rise in temperature. The reaction time is from 1 to about 48 hours, more specifically from 3 to 8 hours, the reaction being considered complete upon disappearance of the Si—H peak from the infrared spectrum of the reaction mixture. When an aprotic solvent is used, the solvent may be removed by stripping or distillation optionally under reduced pressure (vacuum) to provide a substantially solvent-free product.

In one embodiment of the foregoing preparative procedure, 1,1,1-triphenyl-3,3-dialkyl-3-alkenyldisiloxane is obtained by reacting triphonylsilanol with 1,1,3,3-tetraalkyl-1,3-dialkenyldisilazane and/or alkenyldialkylhalosilane wherein each of the alkyl groups and ranges of carbon atoms in said alkyl group are such as those described herein, e.g., methyl, and wherein the alkenyl groups and ranges of carbon atoms in said alkenyl groups are such as those described herein, e.g., vinyl.

In another embodiment herein, there is provided a process of making a triaryl silicon-containing compound (I) which comprises reacting 1,1,1-triphenyl-3,3-dialkyl-3-alkenyldisiloxane in which the alkyl and alkenyl groups are, e.g., methyl and methylene respectively, with a silyl hydride-containing compound to produce 1,1,1-triphenyl-3,3-dialkyl-3-[(silicon-containing group)alkylene]disiloxane.

In another embodiment herein, the reagents can be any triaryl silicon-containing compound (I) that contains one or more silyl hydride functional groups, e.g., one or more of:

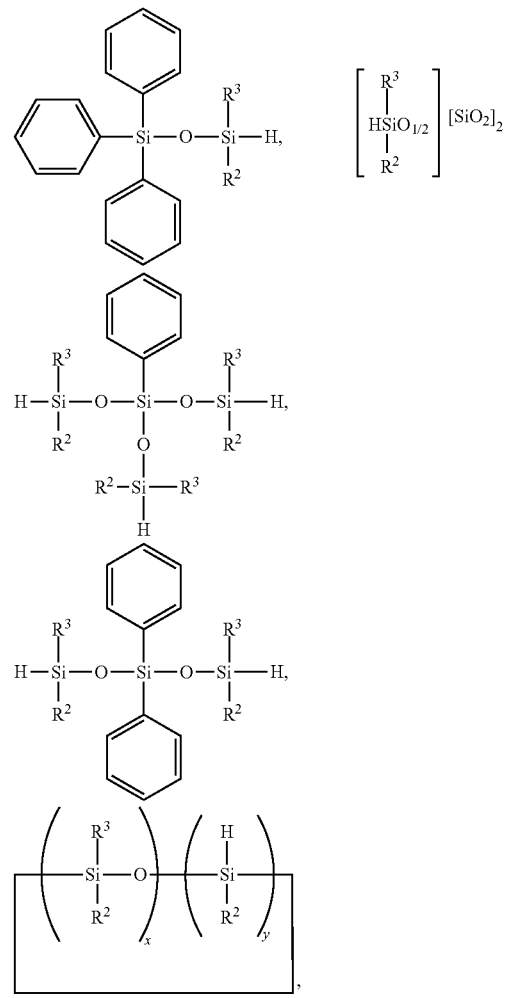

wherein x is 2 and y is 2,

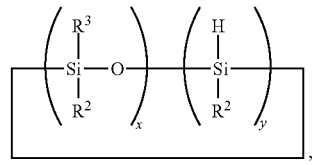

wherein x is 1 and y is 3,

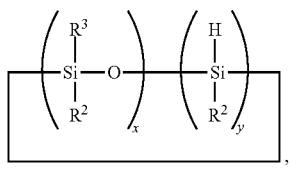

wherein x is 0 and y is 4,

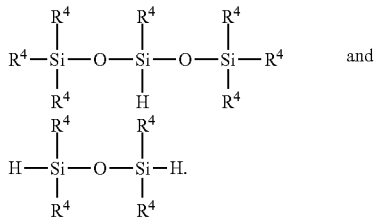

and wherein each $R^2$, $R^3$ and $R^4$ is independently a monovalent hydrocarbon group containing up to about 6 carbon atoms, more specifically up to 4 carbon atoms and most specifically methyl or ethyl and the subscripts have any of the previously defined values.

In yet another embodiment, there is provided a process of making a triaryl silicon-containing compound (I) which comprises reacting a 1,1,1-triphenyl-3,3-dialkyl-3-hydride disiloxane with an alkenyl compound containing from 2 to about 10 carbon atoms, e.g., a linear alkenyl compound, more specifically an alkenyl compound containing from 4 to about 10 carbon atoms, even more specifically from 4 to about 8 carbon atoms, or in another embodiment from 6 to about 8 carbon atoms, and in one embodiment terminally unsaturated at one end and in another embodiment terminally unsaturated at both ends. In cm non-limiting embodiment, the alkenyl compound is 1-octene and in another embodiment 1,7-octadiene.

The processes for making triaryl silicon-containing compound (I) can employ an aprotic solvent, e.g., benzene, toluene, xylene, etc., and mixtures thereof. In one embodiment herein, the amount of solvent can range from about 10 to about 90, more specifically from about 20 to about 70, and still more specifically from about 30 to about 60, weight percent, based on the total weight of the reactants. Where solvent is utilized, it, is preferred that prior to incorporating the product triaryl silicon-containing compound (I) into its host resin, the solvent be largely or completely removed, e.g., by distillation under reduced pressure.

It is also within the scope of the invention to utilize a catalyst in the preparation of triaryl silicon-containing compound (I), e.g., a hydrosilylation catalyst, such as those based on platinum, in particular Karstedt's catalyst, or ruthenium, in known and conventional amounts.

In one embodiment, the process of reacting triphenylsilanol with 1,1,3,3-tetraalkyl-1,3-dialkenyldisilazane and/or alkenyldialkylhalosilane to produce 1,1,1-triphenyl-3,3-dialkyl-3-alkenyldisiloxane comprises reacting triphenylsilanol with 1,1,3,3-tetraalkyl-1,3-dialkenyldisilazane and/or alkenyldialkylhalosilane in a molar ratio of from about 1:0.5 to about 1:10, more specifically from about 1:0.5 to about 1:5 and still more specifically from about 1:0.5 to about 1:2 of triphenylsilanol to the total molar amount of 1,1,3,3-tetraalkyl-1,3-dialkenyldisilazane and/or alkenyldialkylhalosilane.

In one embodiment, the amount of 1,1,3,3-tetraalkyl-1,3-dialkenyldisilazane in a combination of 1,1,3,3-tetraalkyl-1,3-dialkenyldisilazane and alkenyldialkylhalosilane can range from 0 to about 100 mole percent, specifically from 1 to about 100 mole percent, more specifically from about 10 to about 90 mole percent and most specifically from about 20 to about 80 mole percent.

In one embodiment, the process can comprise reacting triphenylsilanol with only 1,1,3,3-tetraalkyl-1,3-dialkenyldisilazane or with only alkenyldialkylhalosilane and with molar ratios of triphenyl to dialkenyldisilazane or alkenyldialkylhalosilane corresponding to those described above for reacting triphenylsilanol with 1,1,3,3-tetraalkyl-1,3-dialkenyldisilazane and/or alkenyldialkylhalosilane.

In another other embodiment, the process of reacting 1,1,1-triphenyl-3,3-dialkyl-3-alkenyldisiloxane with a silyl hydride-containing compound to produce a silicone compound containing at least one silicone moiety comprises employing 1,1,1-triphenyl-3,3-dialkyl-3-alkenyldisiloxane in a molar ratio to hydrogen atoms of silyl hydride-containing compound of from about 100:1 to about 1:1, more specifically from about 50:1 to about 1:1 and still more specifically from about 10:1 to about 1:1.

In yet another embodiment, a process is provided for making a triaryl silicon-containing compound (I) where m is m is 2 to 50 by equilibration of a triaryl silicon-containing compound (I) where m is 1 with a cyclic polysiloxane such as, e.g., 1,1,3,3,5,5,7,7-octamethyltetrasiloxane, or with an acyclic polysiloxane such as, e.g., a hydroxyl-terminated polydimethylsiloxane, in the presence of an equilibration catalyst such as a strong acid or strong base examples of which include sulfuric acid, an acid ion exchange resin, a potassium silanoate compound (K-catalyst) or an ammonium silanoate compound (N-catalyst). The reaction can be carried out at from ambient to elevated temperature. The molar ratio of the triaryl silicon-containing compound (I) where m is 1 to the cyclic or acyclic polysiloxane is determined by the number of —OSi($R^2$)($R^3$) repeat groups that are to be incorporated into the triaryl silicon-containing compound (I).

In one specific embodiment herein, the preparative processes described herein can be conducted at a temperature of from about 0° to about 200° C., more specifically, from about 25° to about 150° C. and still more specifically from about 50° to about 120° C., and at a pressure of from about 0.001 to about 5 atmospheres, more specifically from about 0.07 to about 3 atmospheres and still more specifically from about 0.15 to about 2 atmospheres.

In one specific embodiment herein, the processes described herein can be conducted for a period of from about 1 minute to about 48 hours, more specifically from about 10 minutes to about 24 hours and still more specifically from about 30 minutes to about 10 hours.

It will be understood herein that the definitions of the "R" groups, group G, the subscripts and the other variables can have the same definitions in the process embodiments as these variables have in the composition embodiments.

Any of the conventional or otherwise known procedures for introducing flame retardants into a host resin to provide a flame-retarded resin in accordance with the invention can be utilized herein for combining triaryl silicon-containing compound(s) (I) with the host resin, e.g., mechanical methods such as powder, blending, bulk mixing, extrusion, roll milling, and the like, and chemical methods of attaching triaryl silicon-containing compound (I) to its host resin such as any of those previously mentioned.

As those skilled in the art will readily recognize, the amount of triaryl silicon-containing compound (I) that must be combined with and/or chemically attached to the host resin to impart a significant flame retardant capability thereto may vary over wide limits depending on the nature of the host resin, the particular triaryl silicon-containing compound (I) and whether other flame retardant additive(s) may be utilized, such being determined in a particular case employing routine experimental testing. For most resins, a flame retardant-effective amount of triaryl silicon-containing compound (I) can vary from about 0.1 to about 60, more specifically from about 0.25 to about 30, and still more specifically from about 0.5 to about 10, weight, percent based on the total weight of resin which does not contain the triarylsilyloxy functional group.

In addition to triaryl silicon-containing compound (I), the flame retardant resin composition may also contain at least one conventional or otherwise known flame retardant additive non-limiting examples of which include halogenated flame retardants such as aromatic polybrominated compounds, phosphorus-based flame retardants, e.g., phosphate esters such as triphenyl phosphate, alkylated aromatic phosphate esters such as cresyl phosphate or buylated propylated phenyl phosphate, phosphate-phosponate esters and halogenated phosphate esters such as (tridichloropropyl)phosphate, inorganic flame retardants such as alumina trihydrate, magnesium hydroxide, nanoclays, talc, silica, antidrips such as polytetratrafluoro ethylene (PTFE), potassium salt of diphenyl sulfone sulfunate, and the like, and mixtures thereof. Triaryl silicon-containing compound(s) (I) can be present in admixture with one or more of the foregoing or other known flame retardant additives in widely varying amounts, e.g., from about 10 to about 80, and more specifically from about 10 to about 50, weight percent, based on the total weight of the triaryl silicon-containing compound (I) and the other known flame retardant additive.

The following examples exemplify, but do not limit, the scope of the present invention.

Example 1: Preparation of S1

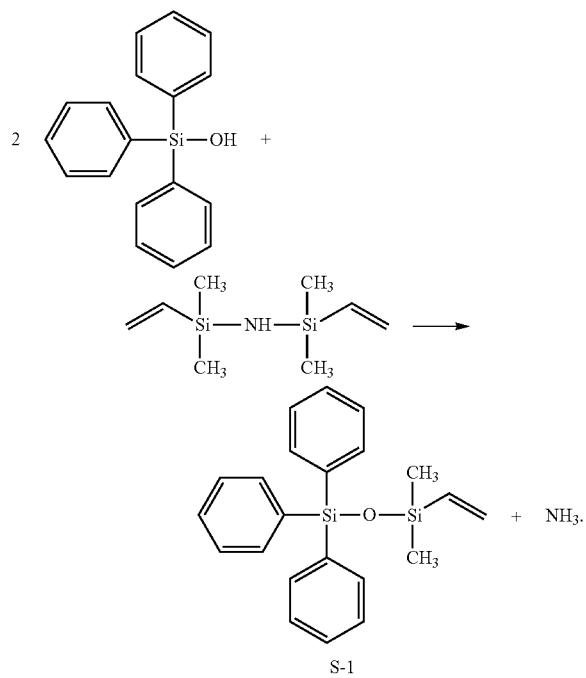

To a stirred solution of 800 grams (2.89 moles) of triphenylsilanol in 1200 grams of toluene at 75° C. was added a mixture of 269 grams (1.45 mole) of 1,1,3,3-tetramethyl-1,3-divinyldisilazane and 88 grams (0.73 mole) of vinyldimethylchlorosilane over a period of 30 minutes. After complete addition, the mixture was stirred for an additional 3 hours at 75° C. to complete a reaction, and then cooled to room temperature. The siloxane in toluene solution was washed 2 times with 1500 ml water. The final separation provided a water layer that was very near neutral in pH. The toluene solution was then heated to 130° C. and stripped at reduced pressure to remove the toluene, leaving 964 grams (94% of theory) of a clear, colorless product with a refractive index, measured at 25° C. of 1.564 and a viscosity of 40 centistokes (cSt). This product was identified as S1 (1,1-dimethyl-3,3,3-triphenyl-3,3-1-vinyldisiloxane) by 1H-NMR and 29Si-NMR analysis.

Example 2: Preparation of Silicone H-1

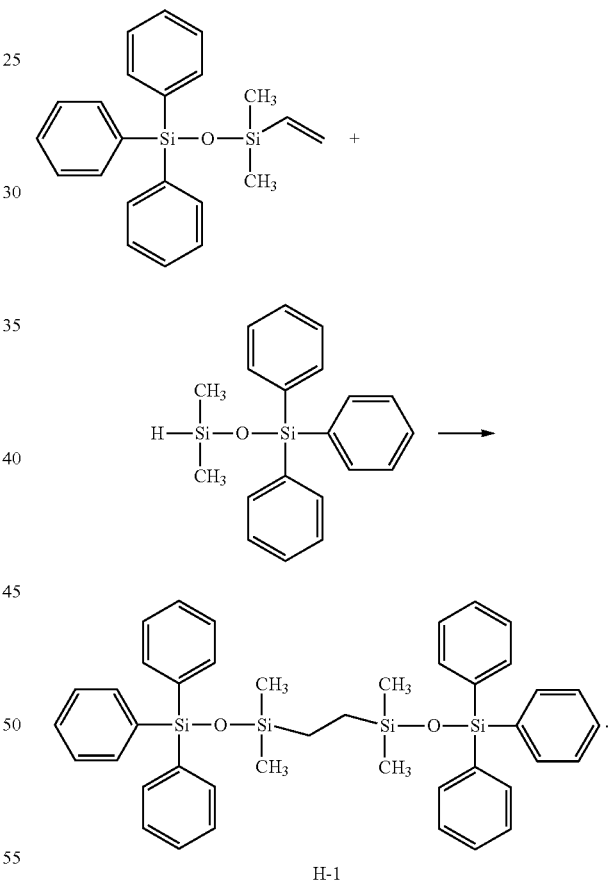

To a stirred mixture of 5 grams (0.014 mole) of S-1 prepared in Example 1 and 10 grams of toluene and platinum catalyst described in Karstedt U.S. Pat. No. 3,775,451 (i.e., platinate(2-), hexachloro-, dihydrogen, (OC-6-11)-, reaction products with 2,4,6,8-tetraethenyl-2,4,6,8-tetramethylcyclotetrasiloxane was used), to provide 5 ppm of Pt catalyst based on a total amount of S-1 and silyl hydride containing compound, 1,1,1-triphenyl-3,3-dimethyl disiloxane, heated to 60° C., was added 4.6 grams (0.014 mole) of 1,1,1-triphenyl-3,3-dimethyl disiloxane over a period of 10 minutes. An exotherm was observed during the addition to about 80° C. After complete, addition, the mixture was stirred for an additional 1 hour at 80° C. to complete a hydrosilylation reaction. The toluene solution was then heated to 120° C. and stripped at reduced pressure to remove the toluene, leaving 9 grams (94% of theory) of a white crystalline product with a refractive index measured at 25° C. of 1.536 in 50% toluene solution and a melting point of 95-99° C. This product was identified as H-1 by 1H-NMR analysis.

Example 3: Preparation of Silicone H-2

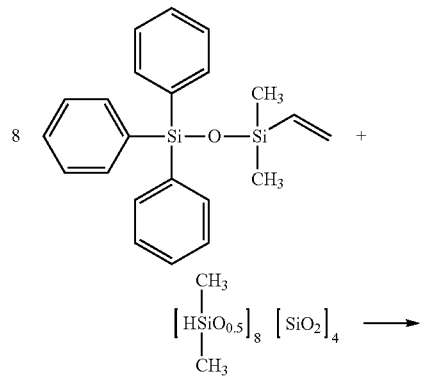

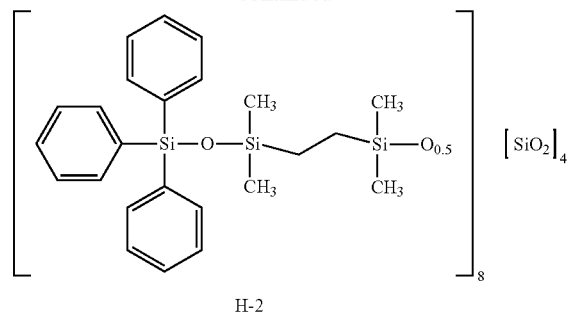

H-2

A procedure similar to Example 2 was performed, except that 2 grams (0.003 mole) of a silyl hydride-containing compound having a general formula of [HSiMe$_2$O$_{0.5}$]$_8$ [SiO$_2$], and 7.8 grams (0.022 mole) of S-1 were used. There was obtained 9.0 grams (92% of theory) of a slightly hazy product with a refractive index measured at 25° C. of 1.556 and a viscosity of 17,000 cP. This product was identified as H-2 by 1H-NMR analysis.

Example 4: Preparation of Silicone H-3

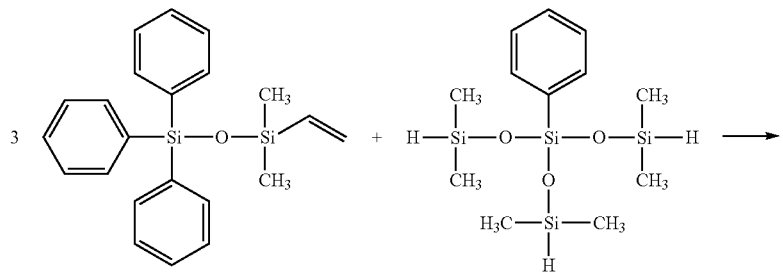

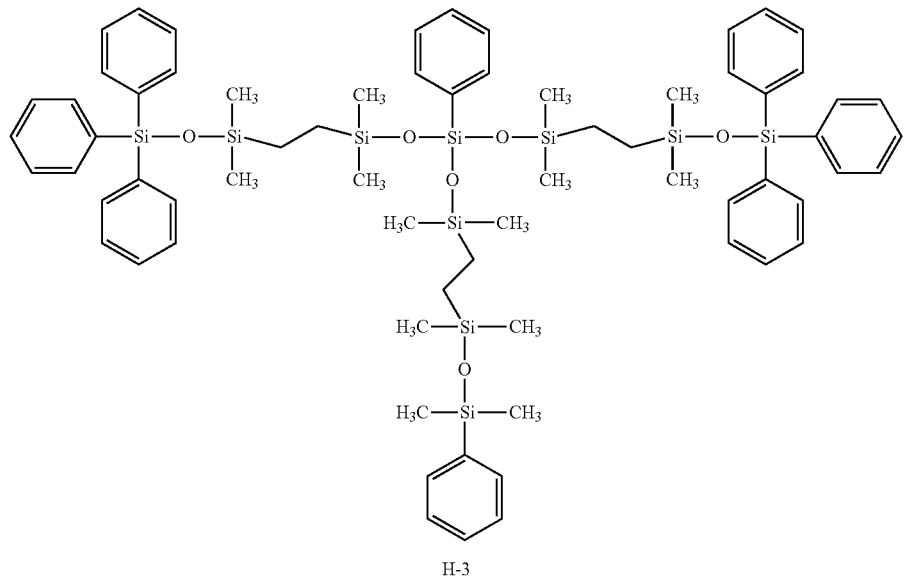

H-3

A procedure similar to Example 2 was performed, except that 40 grams (0.12 mol) of a hydrogen siloxane was used having a formula of PhSi—[OSiMe$_2$H]$_3$ (wherein Ph is phenyl and Me is methyl), 133 grams (0.37 mol) of S-1, 150 grams of toluene. There was obtained 160 grams (92% of theory) of a slightly hazy product, with a refractive index measured at 25° C. of 1.558 and a viscosity of 4400 cP. This product was identified as H-3 by 1H-NMR analysis.

-continued

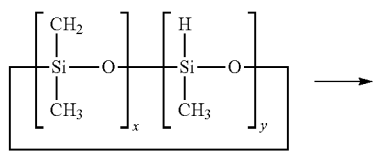

Example 5: Preparation of Silicone H-4

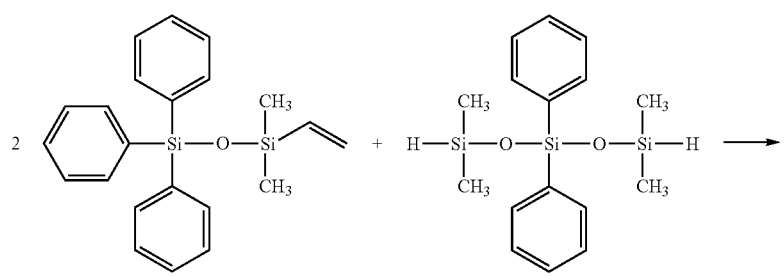

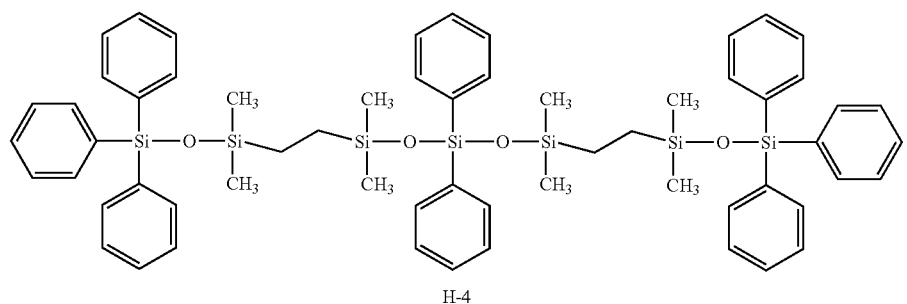

H-4

A procedure similar to Example 2 was performed, except that 4.4 grams (0.013 mole) of a silyl hydride-containing compound having a formula of Ph$_2$Si[OSiMe$_2$H]$_2$ (wherein Ph is phenyl and Me is methyl) and 10 grams (0.028 mole) of S-1. There was obtained 13.5 grams (94% of theory) of a white crystalline product with a refractive index measured at 25° C. of 1.528 in 50% toluene solution and a melting point of 60-65° C. This product was identified as H-4 by 1H-NMR analysis.

Example 6: Preparation of Silicone H-5

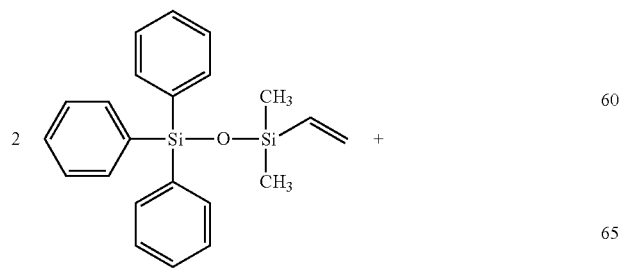

-continued

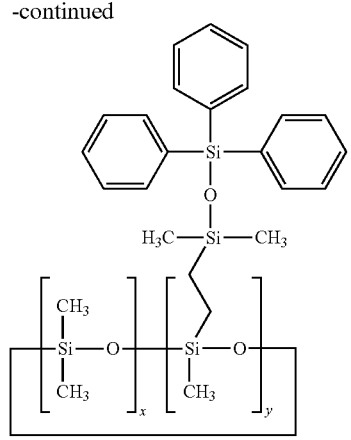

H-5: x = 2, y = 2
H-6: x = 1, y = 3
H-7: x = 0, y = 4

A procedure similar to Example 2 was performed, except that 43 grams (0.16 mole) of a 2,2,4,4,6,8-hexamethylcyclotetrasiloxane 121.5 grams (0.34 mole) of S-1 and 150 grams of toluene were used. There was obtained 160 grams (97% of theory) of a clear, colorless product with a refractive index measured at 25° C. of 1.539 and a viscosity of 1,900 cP. This product was identified as H-5 by 1H-NMR analysis.

Example 7: Preparation of Silicone H-6

A procedure similar to Example 2 was performed, except that 30 grams (0.12 mole) of a 2,2,4,6,8-pentamethylcyclotetrasiloxane, 133.9 grams (0.37 mole) of S-1 and 150 grams of toluene were used. There was obtained 156 grams (95% of theory) of a clear, colorless product with a refractive index measured at 25° C. of 1.555 and a viscosity of 12,900 cP. This product was identified as H-6 by 1H-NMR analysis.

Example 8: Preparation of Silicone H-7

A procedure similar to Example 2 was performed, except that 23 grams (0.10 mole) of a 2,4,6,8-tetramethylcyclotetrasiloxane, 144.8 grams (0.40 mole) of S-1 and 150 grams of toluene were used. There was obtained 160 grams (95% of theory) of a clear, colorless product with a refractive index measured at 25° C. of 1.565 and a viscosity of 56,900 cP. This product was identified as H-7 by 1H-NMR analysis.

Example 9: Preparation of Silicon H-8

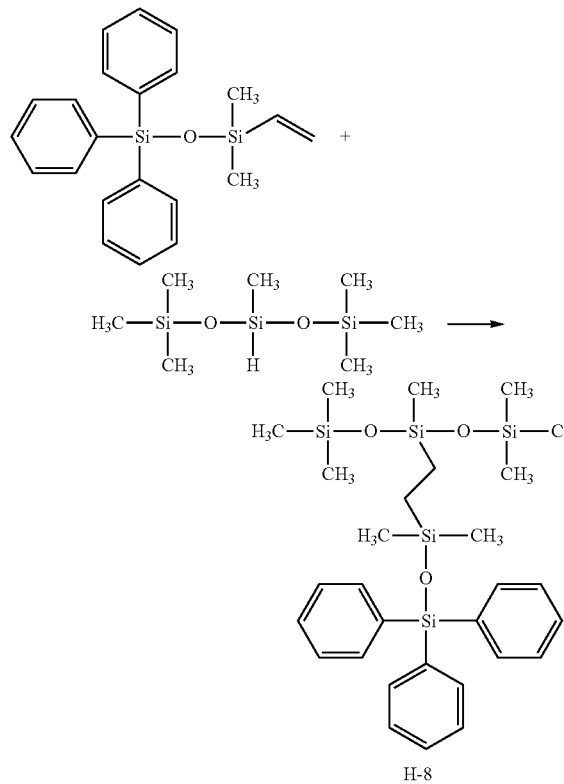

A procedure similar to Example 2 was performed, except that 50 grams (0.23 mol) of a 1,1,1,3,5,5,5-heptamethyltrisiloxane was used as a hydrogen siloxane, 85 grams (0.24 mol) of S-1, 130 grams of toluene. There was obtained 128 grams (95% of theory) of a clear, colorless product with a refractive index measured at 25° C. of 1.507 and a viscosity of 47 cSt. This product was identified as H-8 by 1H-NMR analysis.

Example 10: Preparation of Silicone H-9

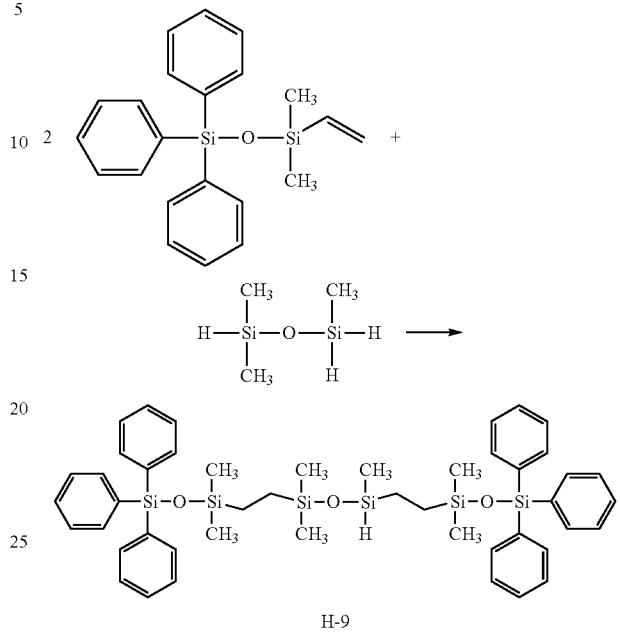

H-9

A procedure similar to Example 2 was performed, except that 20 grams (0.15 mole) of a 1,1,3,3-tetramethydisiloxane, 113 grams (0.31 mole) of S-1 and 130 grams of toluene were used. There was obtained 126 grams (95% of theory) of a clear, colorless product with a refractive index measured at 25° C. of 1.554 and a viscosity of 350 cP. This product was identified as H-9 by 1H-NMR analysis.

The physical properties of S-1 and H-1 to H9 are set forth in Table 1 below:

TABLE 1

Physical Properties Data

| Product | Appearance | Viscosity [Centipoise, 25° C.] | Melting Point [° C.] | Refractive Index [25° C.] |
|---|---|---|---|---|
| S-1 | Clear, colorless | 40* | — | 1.564 |
| H-1 | White crystalline | — | 95-99 | 1.536** |
| H-2 | Slightly hazy | 17,000 | — | 1.556 |
| H-3 | Slightly hazy | 4,400 | — | 1.558 |
| H-4 | White crystalline | — | 60-65 | 1.528** |
| H-5 | Clear, colorless | 1,900 | — | 1.539 |
| H-6 | Clear, colorless | 12,900 | — | 1.555 |
| H-7 | Clear, colorless | 56,900 | — | 1.565 |
| H-8 | Clear, colorless | 47 | — | 1.507 |
| H-9 | Clear, colorless | 350 | — | 1.554 |

*Viscosity of low viscosity product was measured using a Cannon-Fenske viscometer and is reported as in centistokes (cSt). Viscosity of the remaining products was measured using a Vismetron viscometer model no.: VSA-L and is reported as Centipoises.

**Refractive index measurement was carried out using an Abbe Refractomer employing a 50% toluene solution.

Example 11: Preparation of Silicone H-10

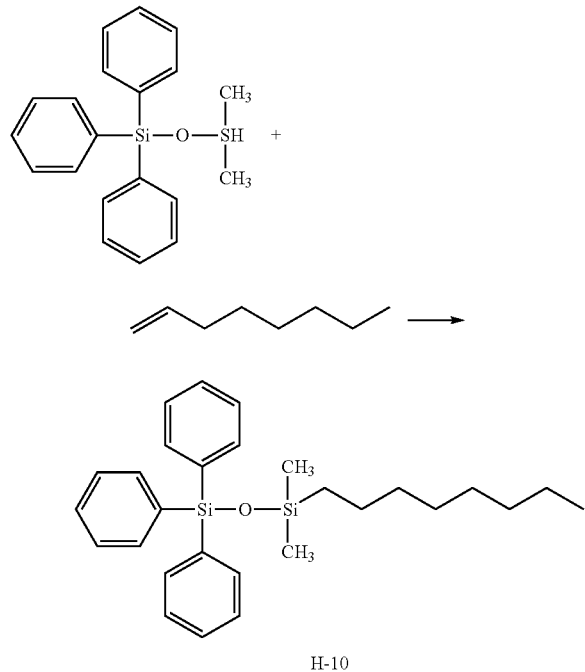

H-10

To a stirred mixture of 1 grams (0.009 mole) of 1-octene, 5 grams of toluene and platinum catalyst as disclosed in U.S. Pat. No. 3,775,452 (platinate(2-), hexachloro-, dihydrogen, (OC-6-11)-, reaction products with 2,4,6,8-tetraethenyl-2,4,6,8-tetramethylcyclotetrasiloxane), to provide 5 ppm of Pt catalyst based on a total amount of 1-octene and 1,1,1-triphenyl-3,3-dimethyldisiloxane at 70° C., was added 2 grams (0.006 mole) of 1,1,1-triphenyl-3,3-dimethyldisiloxane in 2 grams toluene solution over a period of 5 minutes. An exotherm was observed during the addition to about 75° C. After complete addition, the mixture was stirred for an additional 6 hours at 75° C. to complete a hydrosilylation reaction. The toluene solution was then heated to 120° C. and stripped at reduced pressure to remove the toluene and the excess of 1-octene, leaving 2.4 grams (90% of theory) of a clear, pale yellow product with a refractive index measured at 25° C. of 1.536 and a viscosity of 40 cP. This product was identified as H-10 by 1H-NMR analysis.

Example 12: Preparation of TPTES-1, TPTES-2, H-1

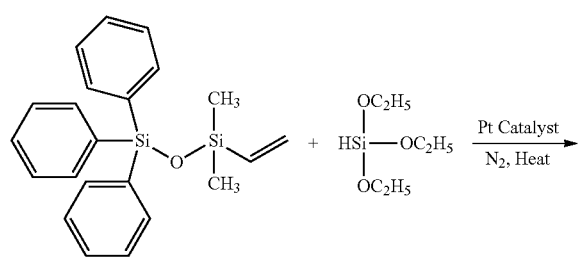

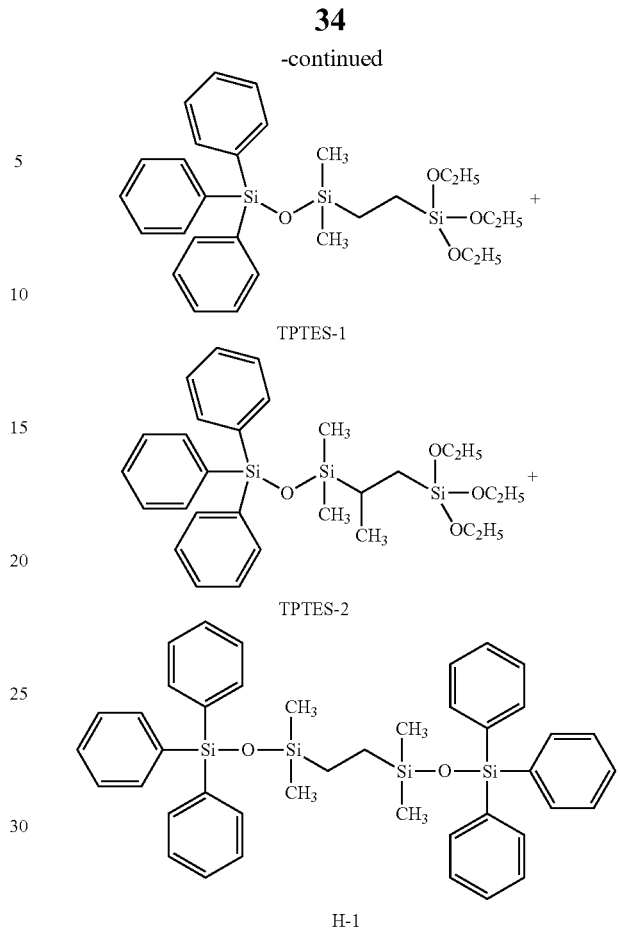

TPTES-1

TPTES-2

H-1

40.82 grams of S-1 (99%) and 36 µl of Karstedt's catalyst containing 1% by weight platinum were dissolved in a dry, 3-neck round bottom fitted with a reflux condenser and addition funnel. To the continuously stirred solution, 18.24 grams of triethoxy silane (TES, 98%) was added dropwise at the room temperature, for a total time of 30 minutes. The reaction temperature was increased to 50° C. for a time of 1 hour and followed by 70° C. for an addition time of 1 hour. The reaction mixture was then heated at to 100° C. with constant stirring for one more hour. The complete consumption of triethoxy silane was confirmed by the absence of a peak related to Si—H at 2200 cm$^{-1}$ in FTIR spectrum of the aliquot. Products are identified as 1,1-dimethyl-3,3,3-triphenyl-1-(2-triethoxysilanyl-ethyl)-disiloxane (TPTES-1), 1,1-dimethyl-3,3,3-triphenyl-1-(1-triethoxysilanyl-ethyl)-disiloxane (TPTES-2), and H-1. These products are collectively referred as TPTES. It was found the concentration of H-1 is largely depending upon the addition process of TES. In the process, described above, the concentration of TPTES-1 and TPTES was 97% and H-1 was 0.6% as determined by GC and GC-MS. The ratio of TPTES-1 to TPTES-2 is 88.3 to 11.7 as calculated using NMR. However, when TES was added dropwise at the temperature of 80° C. for a total time of 40 minutes and continued for a total time of 1 hour, the concentration of TPTES-1 and TPTES was 94% and H-1 was 3% as determined by GC and GC-MS.

In another synthesis, 46.2 grams of S-1 and 40 µl of Karstedt's catalyst containing 1% by weight platinum were dissolved in a dry, 3-neck round bottom fitted with a reflux condenser and, addition funnel. To the continuously stirred solution, 20.97 grams of triethoxy silane was added dropwise at room temperature for a total time of 30 minutes. The reaction temperature was increased to 50° C. for a time of 30 minutes and followed by 90° C. for an addition time of 30 minutes. The reaction mixture was then heated to 130° C. with constant stirring for 5 hours producing a low color product. The complete consumption of triethoxy silane was confirmed by the absence of peak related to Si—H at 2200 cm$^{-1}$ in FTIR spectrum of the aliquot.

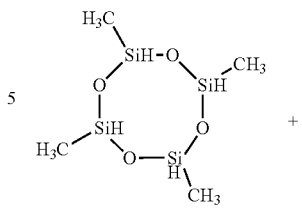

+

Example 13: Preparation of Silicone H-11

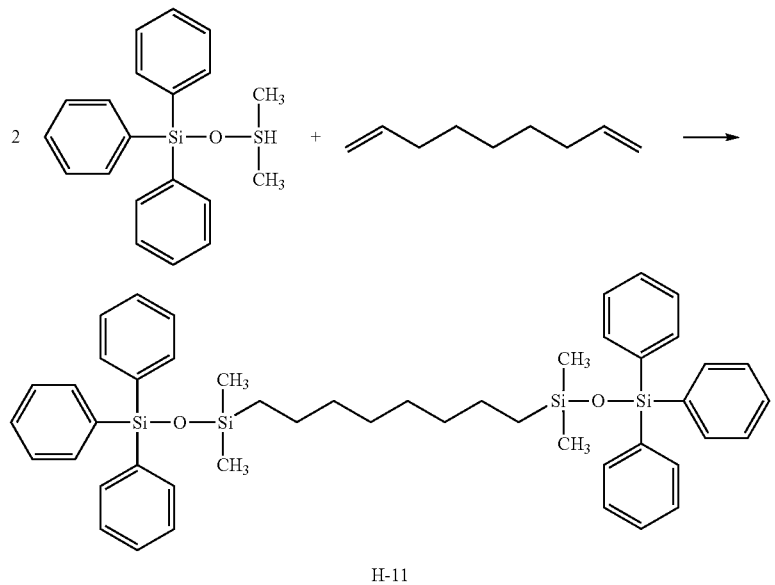

H-11

To a stirred mixture of 0.82 grams (0.007 mol) of 1,7-octadiene, 5 grams of toluene and platinum catalyst shown by Karstedt, U.S. Pat. No. 3,775,452 (platinate(2-), hexachloro)-, dihydrogen, (OC-6-11)-, reaction products with 2,4,6,8-tetraethenyl-2,4,6,8-tetramethylcyclotetrasiloxane), to provide 10 ppm of Pt catalyst based on a total amount of 1,7-octadiene and 1,1,1-triphenyl-3,3-dimethyldisiloxane at 70° C. was added 5 grams (0.015 mole) of 1,1,1-triphenyl-3,3-dimethyldisiloxane in 5 grams of toluene solution over a period of 10 minutes. An exotherm was observed during the addition to about 73° C. After complete addition, the mixture was stirred for an additional 24 hours at 90° C. to complete a hydrosilylation reaction. The toluene solution was then heated to 120° C. and stripped at reduced pressure to remove the toluene, leaving 5.4 grams (93% of theory) of a clear, pale yellow product with a refractive index measured at 25° C. of 1.565 and a viscosity of 1100 cP. This product was identified as H-11 by 1H-NMR analysis.

Example 14: Preparation of Triphenyl Dimethyl Disiloxane-pendant Silicone

A molar excess of the cyclic silicone hydride D$_4$' is hydrosilylated with 1,1-dimethyl-3,3,3-triphenyl-1-vinyldisiloxane in the presence of Karstedt's catalyst under the nitrogen to provide silicone TP-D$_4$. Upon completion of hydrosilylation, as indicated by the disappearance of methylene and methine protons in $^1$H NMR, the excess of D$_4$' is removed by stripping. The synthesis scheme is as follows:

-continued

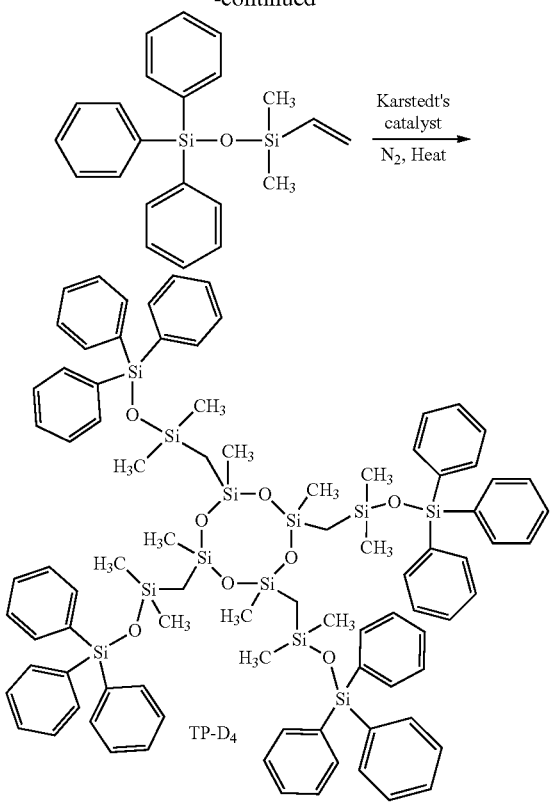

Next, TP-D4 is equilibrated with octamethylcyclotetrasiloxane and 1,1,3,3,3-hexamethyl-disiloxane in the presence of catalyst such as Purolite CT275. This equilibration produces methyl end-functional, triphenyl dimethyl disiloxane pendant silicone as described in the synthesis scheme below:

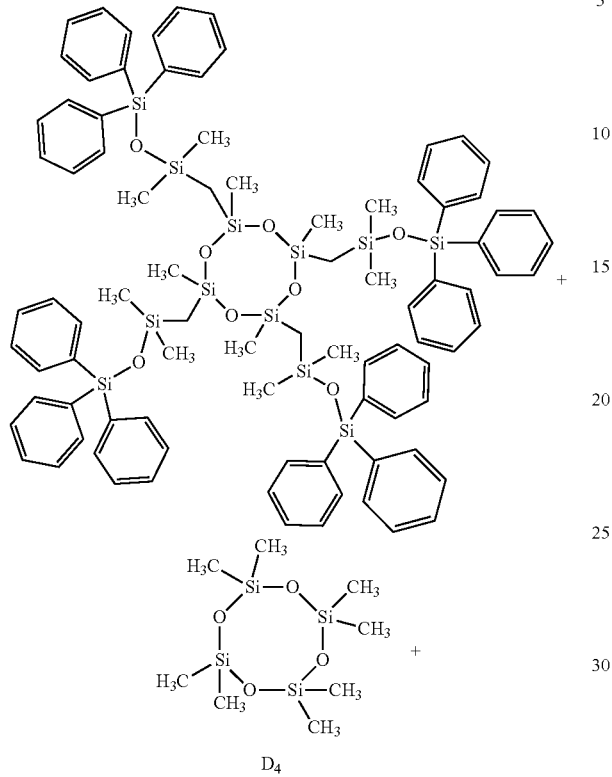

D₄

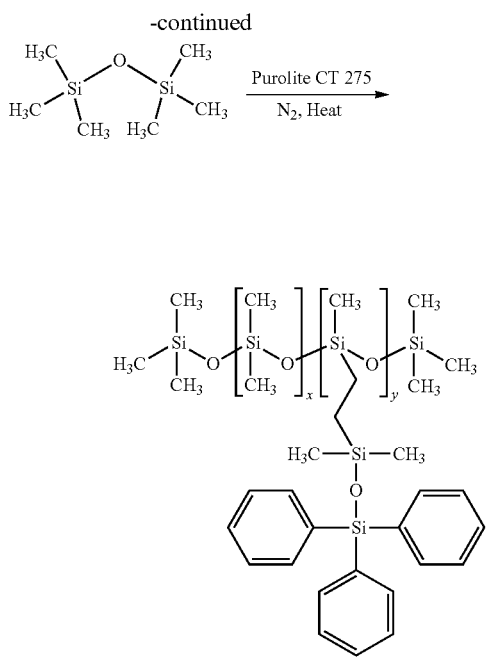

Example 15: Preparation of Triphenyl Dimethyl Disiloxane Terminal and Pendant Silicone Triphenyl dimethyl disiloxane end blocked (terminal) and pendant silicone are produced by utilizing the following reaction scheme:

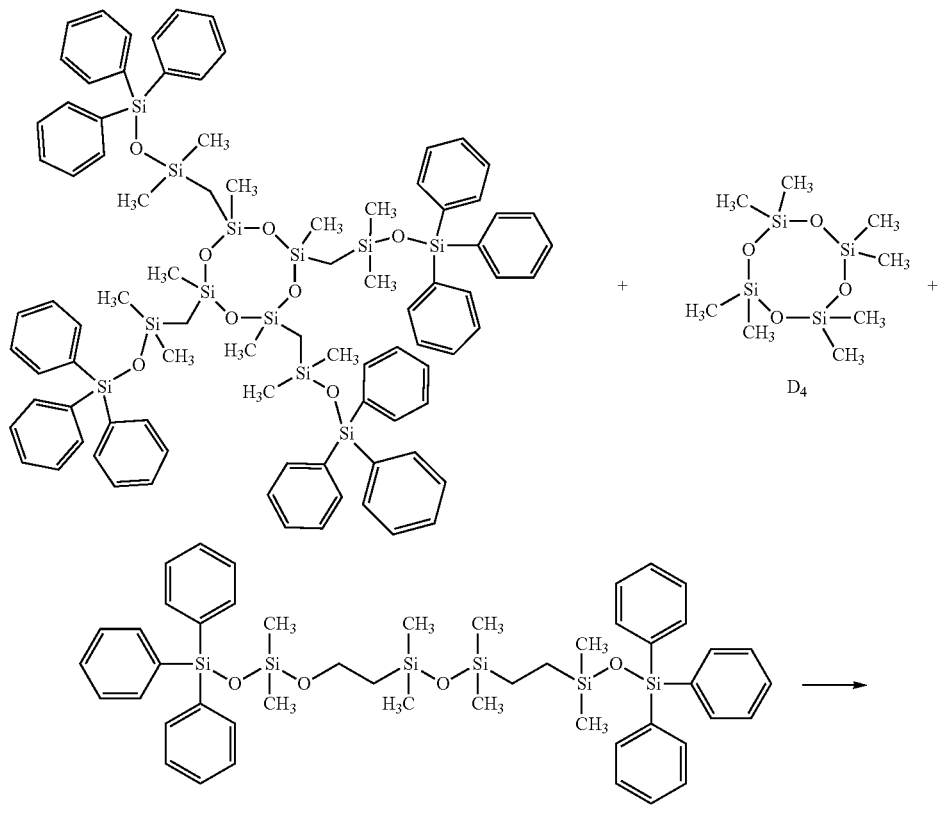

TP-MM-TP

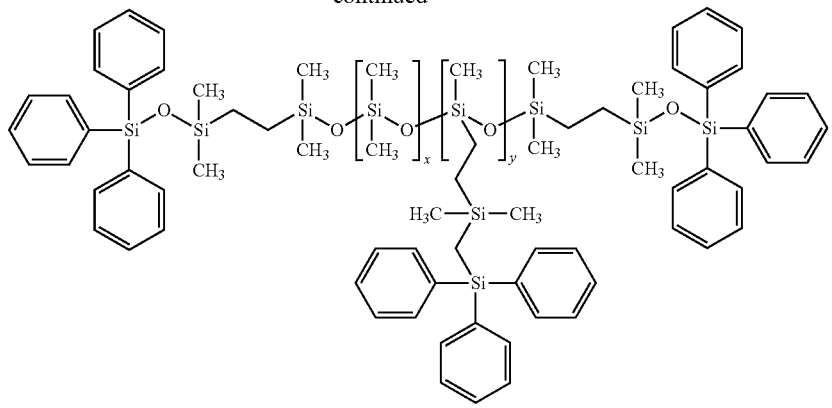

Example 16: Preparation of TP-MM-TP

TP-MM-TP is synthesized according to the following scheme:

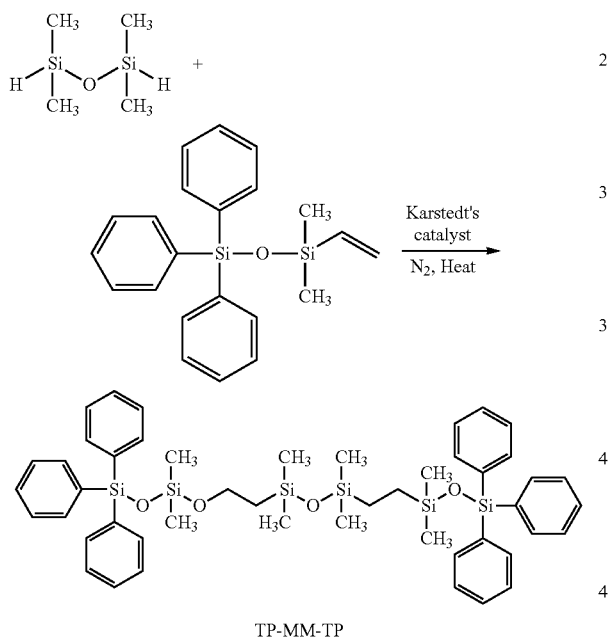

TP-MM-TP

Example 18. Preparation of Triphenyl Dimethyl Disiloxane Terminal and Pendant Silicone Alternatively, 3,3-dimethyl-1,1,1-triphenyl-disiloxane can be hydrosilylated with 1,3,5,7-tetravinyl-1,3,5,7-tetramethylcyclotetrasiloxane and then equilibrated in the presence of octamethylcyclotetrasiloxane and TP-MM-TP.

Example 19: Preparation of Hydride Functional Polydimethylsiloxane Copolymer 4.45 grams of 1,1,3,3-tetramethyldisiloxane (M'M'), 16.72 grams of 1,3,5,7-tetramethylcyclotetrasiloxane, 8.84 grams of octamethylcyclotetrasiloxane were charged in a dry, 3-neck round bottom flask fitted with a reflux condenser. 0.3 grams of Purolite C7275, a catalyst for the equilibration step, were added and stirred under nitrogen overnight at room temperature. Next, the reaction mixture was heated at a temperature of 70° C. and stirred for 14 hours under nitrogen. After completion, the reaction mixture was cooled at room temperature and the catalyst was removed by filtration. The solid content and yield of the product were 85% and 86%, respectively. The synthesis scheme to produce the hydride functional silicone is as follows:

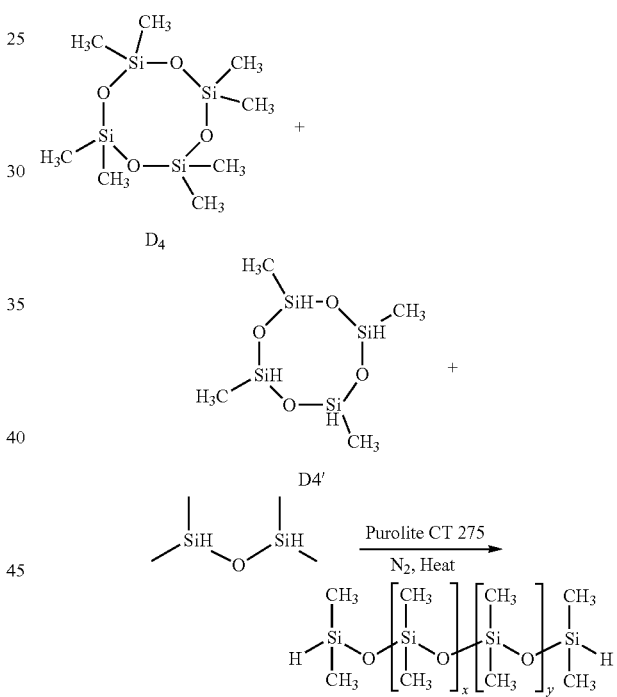

Example 20: Preparation of Triphenyl Dimethyl Disiloxane Containing Polydimethylsiloxane Copolymer (TPPDMS)

12 grams of hydride functional polydimethylsiloxane copolymer of Example 19, 49.98 grams of 1,1-dimethyl-3,3,3-triphenyl-1-vinyl-disiloxane were added and stirrer in a dry, 3-neck round bottom flask under nitrogen. The resulting mixture was hazy. Next, 70 microliters of Karstedt's catalyst was added to the mixture with constant stirring at room temperature. The reaction temperature increased to 80° C. due to the reaction exotherm and the resulting solution became transparent. After 1 hour at 80° C., the reaction temperature was increased to 100° C. and continued for 12 hours until the Si—H peak at 2200 $cm^{-1}$ disappears from FTIR spectrum.

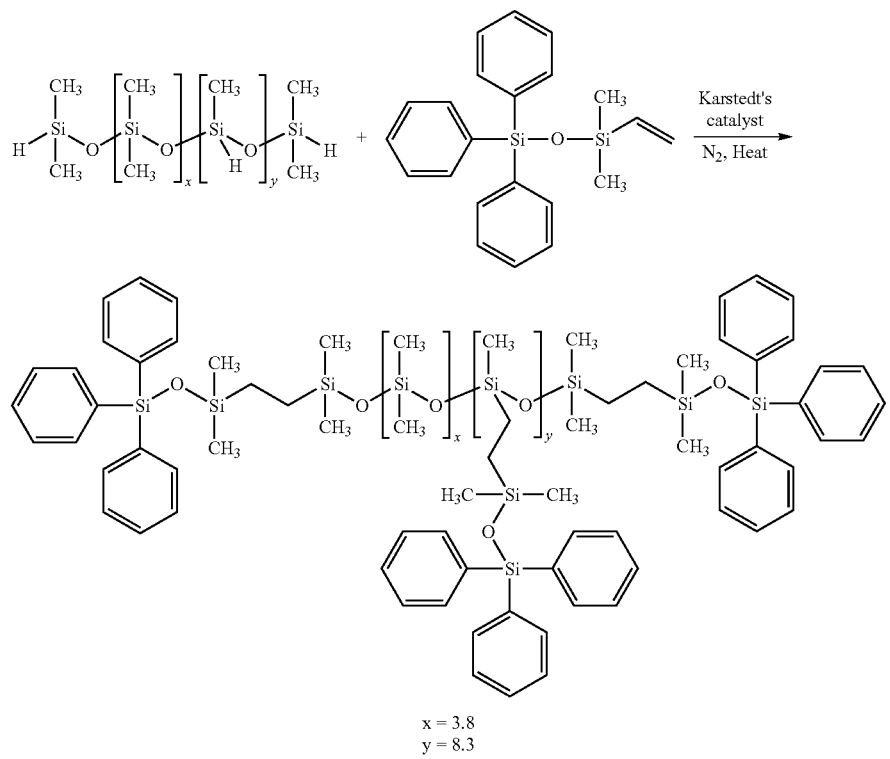

x = 3.8
y = 8.3

Example 21: Polycarbonate Flame Retardant Mixture

This example illustrates the blending of 1,1-dimethyl-3,3,3-triphenyl-3,3-1-vinyldisiloxane (TPDS), H7, and TPTES with polycarbonate. There are two types of pure polycarbonates were used, polycarbonate-1 (LEXAN 121, SABIC Innovative Plastics) and polycarbonate-2 (LEXAN 940A, SABIC innovative Plastics). The physical properties of the resulting blend and their flame retardancy properties are provided below.

The blending of TPDS, H7, and TPTES with polycarbonate was carried out using a microextruder and microinjection mold. Potassium 3-(phenylsulfonyl)benzenesulfonate (KSS) was included as a drip reducing agent as described in Table 2. The flame retardant test was carried out in accordance with the UL-94V 20 mm Vertical burning Test procedure.

Tables 2A and 2B below set forth the compositions of the flame-retarded resin formulations that were blended with polycarbonate to provide test plaques. The polycarbonate was dried by heating at 120° C. for 4 hours before use.

TABLE 2A

Flame-retarded Resin Formulations

| Formulation | Weight % polycarbonate-1 | Weight % polycarbonate-2 | Weight % TPDS | Weight % H-7 | Weight % TPTES | Weight % KSS |
|---|---|---|---|---|---|---|
| 1 | 98.5 | 0 | 1.5 | 0 | 0 | 0 |
| 2 | 97.0 | 0 | 3.0 | 0 | 0 | 0 |
| 3 | 98.1 | 0 | 1.5 | 0 | 0 | 0.4 |
| 4 | 98.5 | 0 | 0 | 1.5 | 0 | 0 |
| 5 | 97.0 | 0 | 0 | 3.0 | 0 | 0 |
| 6 | 0 | 98.5 | 0 | 0 | 1.5 | 0 |
| 7 | 0 | 97.0 | 0 | 0 | 3.0 | 0 |

TABLE 2B

Flame-retarded Resin Formulations

| Formulation | Weight % polycarbonate-2 | Weight % TPTES | Weight % F-2400[a] | Weight % $Sb_2O_3$[b] | Weight % Fyroflex Sol DP[c] | Weight % Nofia C06000[d] | Weight % Bayowet C4[e] |
|---|---|---|---|---|---|---|---|
| 8 | 95.7 | 1.5 | 2 | 0.8 | 0 | 0 | 0 |
| 9 | 84.48 | 1.5 | 0 | 0 | 14.02 | 0 | 0 |

TABLE 2B-continued

| | | | | | Weight % | Weight % | |
| | Weight % | Weight % | Weight % | Weight % | Fyroflex | Nofia | Weight % |
| Formulation | polycarbonate-2 | TPTES | F-2400[a] | Sb$_2$O$_3$[b] | Sol DP[c] | C06000[d] | Bayowet C4[e] |
|---|---|---|---|---|---|---|---|
| 10 | 76.44 | 1.5 | 0 | 0 | 0 | 22.06 | 0 |
| 11 | 98.4 | 1.5 | 0 | 0 | 0 | 0 | 0.1 |

[a]F-2400, brominated epoxy polymer, from ICL Industrial Products
[b]Sb$_2$O$_3$, from Aldridge
[c]Fyroflex Sol DP, from ICL Industrial Products
[d]Nofia C06000, polyphosphonate-co-carbonates, from FRX Polymers
[e]Bayowet C4, from Lanxess The pre-blended mixture of dry polycarbonate and TPP-DMS were extruded using a micro-extruder from Xplore Instruments. The temperature profiles of the micro-extruder at feeding zone, mixing zone, and die head zone were 250° C., 330° C., and 330° C., respectively. The microextruder included a recycle valve attached to the die head. When the recycle valve was opened, the molten polymer was forced to pass through a heated channel that connected to the feed zone. By opening the recycle valve for a certain time, molten polymer could be circulated between the feed zone and the die head zone of the micro-extruder providing better mixing of components. Once the desired amount of mixing and reaction was achieved, the recycle valve could be closed allowing the molten polymer to emerge from the die as a single strand. The transfer device and injection mold were set at a temperature of 335° C. and 80° C. respectively. The transfer device of the micro-injection mold was used to collect the polymer melt from the micro-extruder and transfer the molten polymer to various injection molds. Plaques of 127 mm×13 mm×1.65 mm were used for UL 94V testing.

The optical transparency and haze of 3 mm, 2 mm, and 1 mm thick polycarbonate plaques were evaluated using Haze Gard from BYK according to the ASTM D1003 test procedure, the results 1% transparency and % haze) being presented in Table 3 below:

TABLE 3

Results of Optical Transparency and Haze Testing

| | 3 mm | | 2 mm | | 1 mm | |
|---|---|---|---|---|---|---|
| Test Plaque | % Transparency | % Haze | % Transparency | % Haze | % Transparency | % Haze |
| polycarbonate-1 | 86.20 ± 0.17 | 7.5 ± 0.04 | 88.13 ± 0.15 | 4.5 ± 0.10 | 90.0 ± 0.17 | 2.43 ± 0.11 |
| polycarbonate-2 | 86.6 ± 0.06 | 6.63 ± 0.2 | 88.1 ± 0.2 | 7.7 ± 0.5 | 89.8 ± 0.06 | 4.9 ± 0.06 |
| Formulation 1 | 86.03 ± 0.37 | 5.9 ± 0.09 | 87.77 ± 0.11 | 4.89 ± 0.05 | 89.57 ± 0.20 | 2.74 ± 0.22 |
| Formulation 2 | 87.45 ± 0.06 | 6.5 ± 0.03 | 88.97 ± 0.06 | 5.85 ± 0.07 | 90.4 ± 0.2 | 3.21 ± 0.54 |
| Formulation 3 | 84.6 ± 0.26 | 12.53 ± 0.32 | 87.5 ± 0.26 | 7.56 ± 0.04 | 89.8 ± 0.10 | 3.39 ± 0.26 |
| Formulation 4 | 87.5 ± 0.34 | 4.99 ± 0.05 | 88.7 ± 0.1 | 5.52 ± 0.12 | 89.87 ± 0.11 | 3.07 ± 0.21 |
| Formulation 5 | 87.9 ± 0.1 | 5.51 ± 0.11 | 89.13 ± 0.30 | 5.27 ± 0.38 | 90.36 ± 0.15 | 2.14 ± 0.17 |
| Formulation 6 | 87.1 ± 0.1 | 7.3 ± 0.02 | 88.8 ± 0.1 | 6.5 ± 0.03 | 90.3 ± 0.05 | 5.38 ± 0.5 |
| Formulation 7 | 87.7 ± 0.1 | 7.1 ± 0.05 | 88.9 ± 0.1 | 6.8 ± 0.1 | 90.4 ± 0.05 | 6.7 ± 0.2 |
| Formulation 8 | 18.9 ± 0.3 | 100 | 31.4 ± 0.05 | 100 | 47.5 ± 0.2 | 100 |
| Formulation 9 | 86.5 ± 0.05 | 23.4 | 88 ± 0.1 | 16.2 ± 0.5 | 89.7 ± 0.1 | 14.9 ± 0.2 |
| Formulation 10 | 80.7 ± 0.1 | 7.7 ± 0.02 | 83.9 ± 0.05 | 10.3 ± 0.1 | 87.7 ± 0.1 | 8.6 ± 0.3 |
| Formulation 11 | 77.9 ± 0.2 | 25.1 ± 1.4 | 82.6 ± 0.1 | 15.4 ± 0.5 | 87 ± 0.06 | 7.03 ± 0.3 |

Flame retardant testing of the silicone blended polycarbonate composite was carried out according to UL-94V 20 mm Vertical Burning Test procedure. Rectangular polycarbonate plaques of 125 mm length, 13 mm width, 1.65 mm thickness were made by injection molding. The plaques were conditioned at a temperature of 23° C. and relative humidity of 50% for a minimum of 48 hours before test. The results of the test are set forth in Table 4:

TABLE 4

Results of Flame Retardant Testing

| | Plaque 1 | Plaque 2 | Plaque 3 | Plaque 4 | Plaque 5 |
|---|---|---|---|---|---|
| polycarbonate-1 | | | | | |
| Duration Of Flaming After First Application (T1) (sec) | 12 | 12 | 5 | 9 | 6 |

TABLE 4-continued

Results of Flame Retardant Testing

| | Plaque 1 | Plaque 2 | Plaque 3 | Plaque 4 | Plaque 5 |
|---|---|---|---|---|---|
| Duration Of Flaming After Second Application (T2) (sec) | 10 | 2 | 6 | 6 | 8 |
| Total Afterflame (T1 + T2) (sec) | | | 76 | | |
| Afterglow after second flame application (T3) (sec) | 0 | 0 | 0 | 0 | 0 |
| Duration of flaming/glowing after second application (T2 + T3) (sec) | 10 | 2 | 6 | 6 | 8 |
| Sample flamed or glowed on a holding clamp | No | No | No | No | No |
| Sample ignited surgical cotton | Yes | Yes | Yes | Yes | Yes |
| polycarbonate-2 | | | | | |
| Duration Of Flaming After First Application (T1) (sec) | 2 | 3 | 2 | 5 | 2 |
| Duration Of Flaming After Second Application (T2) (sec) | 3 | 1 | 1 | 3 | 3 |
| Total Afterflame (T1 + T2) (sec) | | | 25 | | |
| Afterglow after second flame application (T3) (sec) | 0 | 0 | 0 | 0 | 0 |
| Duration of flaming/glowing after second application (T2 + T3) (sec) | 3 | 1 | 1 | 3 | 3 |
| Sample flamed or glowed on a holding clamp | No | No | No | No | No |
| Sample ignited surgical cotton | No | Yes | Yes | Yes | No |
| Formulation 1 | | | | | |
| Duration Of Flaming After First Application (T1) (sec) | 10 | 10 | 6 | 8 | 7 |
| Duration Of Flaming After Second Application (T2) (sec) | 2 | 4 | 5 | 1 | 2 |
| Total Afterflame (T1 + T2) (sec) | | | 55 | | |
| Afterglow after second flame application (T3) (sec) | 0 | 0 | 0 | 0 | 0 |
| Duration of flaming/glowing after second application (T2 + T3) (sec) | 2 | 4 | 5 | 1 | 2 |
| Sample flamed or glowed on a holding clamp | No | No | No | No | No |
| Sample ignited surgical cotton | Yes | Yes | Yes | Yes | Yes |
| Formulation 2 | | | | | |
| Duration Of Flaming After First Application (T1) (sec) | 9 | 8 | 10 | 2 | 8 |
| Duration Of Flaming After Second Application (T2) (sec) | 2 | 4 | 5 | 2 | 7 |
| Total Afterflame (T1 + T2) (sec) | | | 57 | | |
| Afterglow after second flame application (T3) (sec) | 0 | 0 | 0 | 0 | 0 |
| Duration of flaming/glowing after second application (T2 + T3) (sec) | 2 | 4 | 5 | 2 | 7 |
| Sample flamed or glowed on a holding clamp | No | No | No | No | No |
| Sample ignited surgical cotton | Yes | Yes | Yes | Yes | Yes |
| Formulation 3 | | | | | |
| Duration Of Flaming After First Application (T1) (sec) | 5 | 1 | 2 | 7 | 5 |
| Duration Of Flaming After Second Application (T2) (sec) | 2 | 2 | 6 | 2 | 5 |
| Total Afterflame (T1 + T2) (sec) | | | 37 | | |
| Afterglow after second flame application (T3) (sec) | 0 | 0 | 0 | 0 | 0 |
| Duration of flaming/glowing after second application (T2 + T3) (sec) | 2 | 2 | 6 | 2 | 5 |
| Sample flamed or glowed on a holding clamp | No | No | No | No | No |
| Sample ignited surgical cotton | No | No | No | No | No |
| Formulation 4 | | | | | |
| Duration Of Flaming After First Application (T1) (sec) | 5 | 5 | 5 | 6 | 6 |

TABLE 4-continued

Results of Flame Retardant Testing

|  | Plaque 1 | Plaque 2 | Plaque 3 | Plaque 4 | Plaque 5 |
|---|---|---|---|---|---|
| Duration Of Flaming After Second Application (T2) (sec) | 3 | 3 | 5 | 6 | 6 |
| Total Afterflame (T1 + T2) (sec) | | | 50 | | |
| Afterglow after second flame application (T3) (sec) | 0 | 0 | 0 | 0 | 0 |
| Duration of flaming/glowing after second application (T2 + T3) (sec) | 3 | 3 | 5 | 6 | 6 |
| Sample flamed or glowed on a holding clamp | No | No | No | No | No |
| Sample ignited surgical cotton | Yes | Yes | Yes | Yes | Yes |
| Formulation 5 | | | | | |
| Duration Of Flaming After First Application (T1) (sec) | 4 | 5 | 7 | 1 | 5 |
| Duration Of Flaming After Second Application (T2) (sec) | 6 | 2 | 1 | 5 | 3 |
| Total Afterflame (T1 + T2) (sec) | | | 39 | | |
| Afterglow after second flame application (T3) (sec) | 0 | 0 | 0 | 0 | 0 |
| Duration of flaming/glowing after second application (T2 + T3) (sec) | 6 | 2 | 1 | 5 | 3 |
| Sample flamed or glowed on a holding clamp | No | No | No | No | No |
| Sample ignited surgical cotton | Yes | Yes | Yes | Yes | Yes |
| Formulation 6 | | | | | |
| Duration Of Flaming After First Application (T1) (sec) | 4 | 4 | 3 | 3 | 3 |
| Duration Of Flaming After Second Application (T2) (sec) | 1 | 2 | 3 | 1 | 1 |
| Total Afterflame (T1 + T2) (sec) | | | 25 | | |
| Afterglow after second flame application (T3) (sec) | 0 | 0 | 0 | 0 | 0 |
| Duration of flaming/glowing after second application (T2 + T3) (sec) | 1 | 2 | 3 | 1 | 1 |
| Sample flamed or glowed on a holding clamp | No | No | No | No | No |
| Sample ignited surgical cotton | No | No | No | Yes | Yes |
| Formulation 7 | | | | | |
| Duration Of Flaming After First Application (T1) (sec) | 3 | 2 | 3 | 2 | 1 |
| Duration Of Flaming After Second Application (T2) (sec) | 1 | 2 | 2 | 2 | 3 |
| Total Afterflame (T1 + T2) (sec) | | | 21 | | |
| Afterglow after second flame application (T3) (sec) | 0 | 0 | 0 | 0 | 0 |
| Duration of flaming/glowing after second application (T2 + T3) (sec) | 1 | 2 | 2 | 2 | 3 |
| Sample flamed or glowed on a holding clamp | No | No | No | No | No |
| Sample ignited surgical cotton | No | No | No | No | No |
| Formulation 8 | | | | | |
| Duration Of Flaming After First Application (T1) (sec) | 1 | 1 | 2 | 1 | 1 |
| Duration Of Flaming After Second Application (T2) (sec) | 1 | 1 | 0 | 2 | 1 |
| Total Afterflame (T1 + T2) (sec) | | | 11 | | |
| Afterglow after second flame application (T3) (sec) | 0 | 0 | 0 | 0 | 0 |
| Duration of flaming/glowing after second application (T2 + T3) (sec) | 1 | 1 | 0 | 2 | 1 |
| Sample flamed or glowed on a holding clamp | No | No | No | No | No |
| Sample ignited surgical cotton | No | No | No | No | No |
| Formulation 9 | | | | | |
| Duration Of Flaming After First Application (T1) (sec) | 2 | 3 | 1 | 1 | 1 |

TABLE 4-continued

Results of Flame Retardant Testing

|  | Plaque 1 | Plaque 2 | Plaque 3 | Plaque 4 | Plaque 5 |
|---|---|---|---|---|---|
| Duration Of Flaming After Second Application (T2) (sec) | 1 | 1 | 1 | 1 | 1 |
| Total Afterflame (T1 + T2) (sec) |  |  | 13 |  |  |
| Afterglow after second flame application (T3) (sec) | 0 | 0 | 0 | 0 | 0 |
| Duration of flaming/glowing after second application (T2 + T3) (sec) | 1 | 1 | 1 | 1 | 1 |
| Sample flamed or glowed on a holding clamp | No | No | No | No | No |
| Sample ignited surgical cotton | No | No | No | No | No |
| Formulation 10 |  |  |  |  |  |
| Duration Of Flaming After First Application (T1) (sec) | 6 | 9 | 6 | 1 | 3 |
| Duration Of Flaming After Second Application (T2) (sec) | 1 | 2 | 2 | 1 | 2 |
| Total Afterflame (T1 + T2) (sec) |  |  | 33 |  |  |
| Afterglow after second flame application (T3) (sec) | 0 | 0 | 0 | 0 | 0 |
| Duration of flaming/glowing after second application (T2 + T3) (sec) | 1 | 2 | 2 | 1 | 2 |
| Sample flamed or glowed on a holding clamp | No | No | No | No | No |
| Sample ignited surgical cotton | No | No | No | Yes | No |
| Formulation 11 |  |  |  |  |  |
| Duration Of Flaming After First Application (T1) (sec) | 3 | 2 | 2 | 1 | 1 |
| Duration Of Flaming After Second Application (T2) (sec) | 3 | 1 | 3 | 1 | 5 |
| Total Afterflame (T1 + T2) (sec) |  |  | 22 |  |  |
| Afterglow after second flame application (T3) (sec) | 0 | 0 | 0 | 0 | 0 |
| Duration of flaming/glowing after second application (T2 + T3) (sec) | 3 | 1 | 3 | 1 | 5 |
| Sample flamed or glowed on a holding clamp | No | No | No | No | No |
| Sample ignited surgical cotton | No | No | Yes | Yes | No |

In another set of experiments, TPTES was blended with a series of polymers such as polypropylene, polyethylene terephthalate (opaque, 30% glass particles as reinforcer), polymethylmethacrylate (transparent. Mw=120,000), polystyrene (transparent, Mw=35,000), poly(styrene-co-acrylonitrile) (transparent, Mw=165,000, acrylonitrile 25 wt. %), polyamide (Trogamid CX7323, transparent), polyetherimide (transparent, melt index=9 g/10 min at 337° C./6.6 kg), and polysulfone (transparent, Mw=35,000, Mn=16,000) at a loading of 5 weight and the optical transparency and the flame retardancy of the blended plaques were evaluated. The optical properties of such plaques were reported at a plaque thickness of 1.6 mm. The difference between the transparency of pure polymer and pure polymer/TPTES blend was represented as ΔT. The difference between the have of pure polymer/TPTES blend and pure polymer was represented as ΔH. Results showed that the addition of 5 weight % TPTES, there is no negative impact on the optical properties of polymethylmethacrylate polystyrene, poly(styrene-co-acrylonitrile), polyamide, and polysulfone. The ΔT and ΔH values of resulting transparent plaques are shown in the following Table.

TABLE 5

Results of Optical Transparency and Haze Testing

| Polymer | ΔT | ΔH |
|---|---|---|
| Polypropylene | 4.9 | −1.2 |
| Polymethylmethacrylate | −0.9 | −0.3 |
| Poly(styrene-co-acrylonitrile) | −0.5 | −0.8 |
| Polyamide | 0.8 | 16.2 |
| Polysulfone | 3.4 | 6.7 |

Example 22: Preparation of a Mixture of 1,1,1-Triphenyl-3,3-Dimethyl-3-Hydroxydisiloxane (TPDHDS) and 1,1,1,5,5,5-1-Hexaphenyl-3,3-Dimethyltrisiloxane (HPDTS)

A mixture of 1,1,1-triphenyl-3, 3-dimethyl-3-hydroxydisiloxane (TPDHDS) and 1,1,1,5,5,5-hexaphenyl-3,3-dimethyltrisiloxane (HPDTS) was prepared.

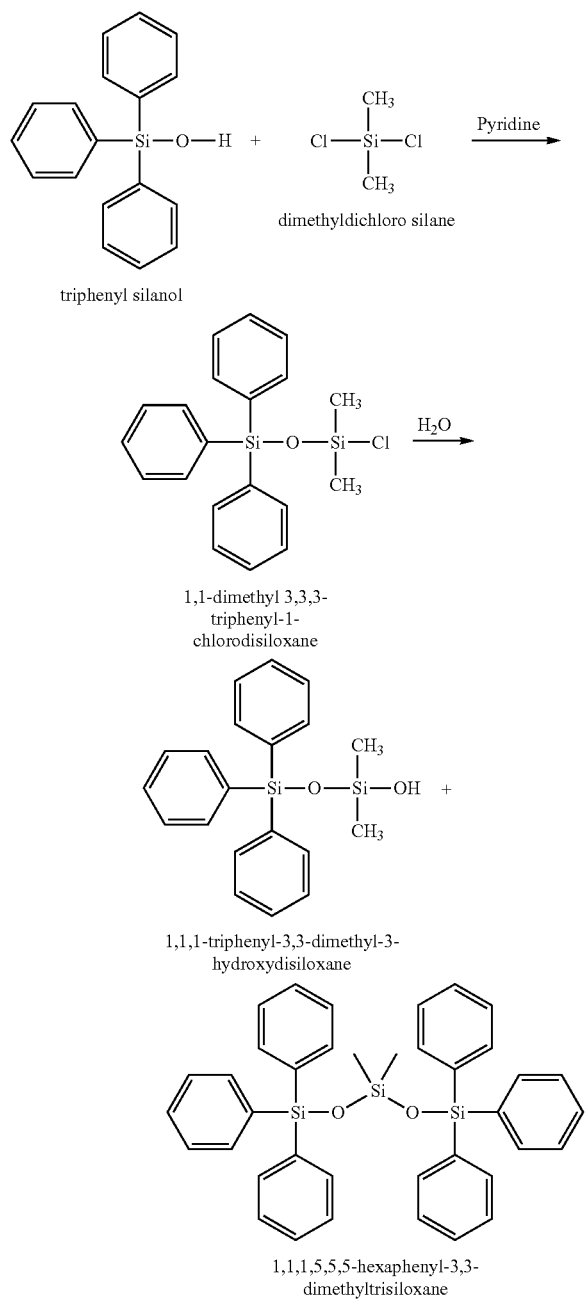

1,1,1,5,5,5-hexaphenyl-3,3-dimethyltrisiloxane

To a stirred solution of 37.4 grams (0.29 mole) dimethyldichlorosilane in 170 grams toluene at 8° C. was added a solution of 80 grams (0.29 mole) triphenylsilanol, 25.1 grams (0.32 mole) pyridine and 40 grams toluene over a period of 30 minutes. An exotherm was observed during the addition to about 30° C. After complete addition, the mixture was stirred for an additional 2 hours below 30° C. followed by an addition of 100 ml water to initiate hydrolysis. The reaction mixture was stirred for 1 hour at ambient temperature. The siloxane in toluene solution was washed twice with 500 ml water. Final separation provided a water layer that was very near neutral in pH. The toluene solution was then heated to 130° C. and stripped at reduced pressure to remove toluene leaving 90 grams of a white, solid product with a melting point of 71~85° C. The product was identified as a mixture of 1,1,1-triphenyl-3,3-dimethyl-3-hydroxydisilox- ane (TPDHDS) (85 wt %) and 1,1,1,5,5,5-hexaphenyl-3,3-dimethyltrisiloxane (HPDTS) (15 wt %) by 1H-NMR and 29Si-NMR analysis.

Example 19: Preparation of 1,1,1-Triphenyl-3,3,3-Trimethyldisiloxane (TPTDS)

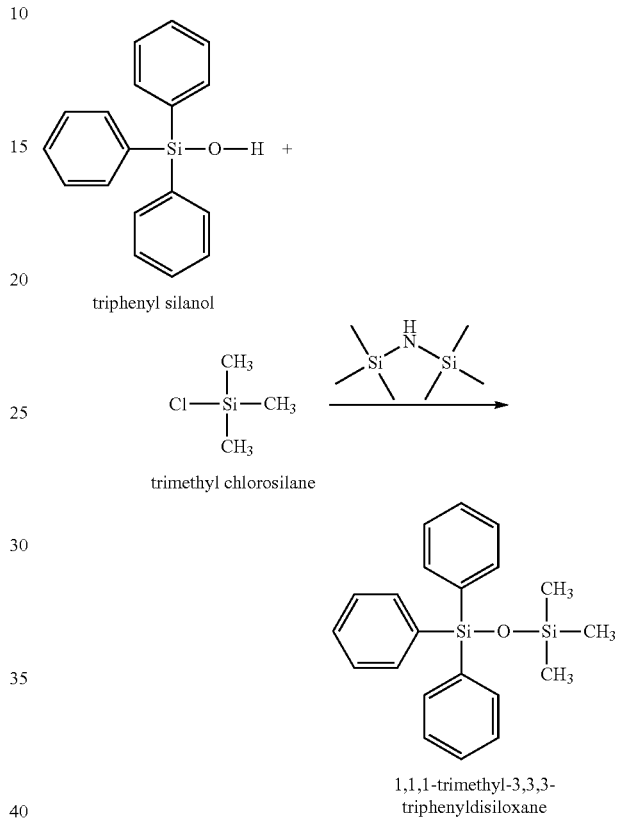

1,1,1-trimethyl-3,3,3-triphenyldisiloxane

To a stirred solution of 330 grams (1.19 mol) triphenylsilanol in 500 grams toluene at 75° C. was added a mixture of 116 grams (0.72 mol) 1,1,1,3,3,3-hexamethyldisilazane and 39 grams (0.36 mol) trimethylchlorosilane over a period of 20 minutes. After complete addition, the mixture was stirred for an additional 3 hours at 75° C. to complete the reaction followed by cooling to ambient temperature. The siloxane in, toluene solution was washed twice with 600 ml water. Final separation provided a water layer that was very near neutral in pH. The toluene solution was then heated to 130° C. and stripped at reduced pressure to remove toluene leaving 372 grams (89.7% of theory) of a white solid product with an n25/D=1.558 and a melting point of 50~52° C. The product was identified as 1,1,1-triphenyl-3,3,3-trimethyldisiloxane (TPTDS) by 1H-NMR analysis.

Example 23: Preparation of 1,1,1,3-Tetraphenyl-3,3-Dimethyldisiloxane (TPDMDS)

1,1,1,3-Tetraphenyl-3,3-dimethyldisiloxane (TPDMDS) was prepared.

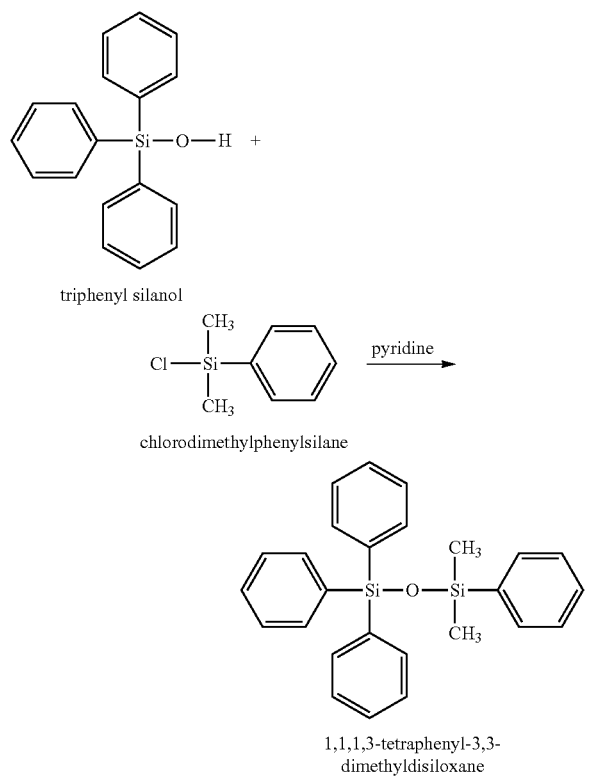

triphenyl silanol chlorodimethylphenylsilane 1,1,1,3-tetraphenyl-3,3-dimethyldisiloxane To a stirred solution of 77 grams (0.28 mole) triphenylsilanol, 25.5 grams (0.32 mole) pyridine and 110 grams toluene at 3° C. was added 50 grams (0.29 mole) chlorodimethylphenylsilane over a period of 20 minutes. An exotherm was observed during the addition to about 20° C. After complete addition, the reaction mixture was stirred for an additional 2 hours at ambient temperature. The siloxane in toluene solution was washed twice with 500 ml water. Final separation provided a water layer that was very near neutral in pH. The toluene solution was then heated to 130° C. and stripped at reduced pressure to remove toluene leaving 100 grams (87.2% of theory) of a white solid product with an n25/D=1.586 and a melting point of 44~49° C. The product was identified as 1,1,1,3-tetraphenyl-3,3-dimethyldisiloxane (TPDMDS) by 1H-NMR analysis.

Example 24: Preparation of 1,1,1,3,3,3-Hexaphenyldisiloxane (HPDS)

1,1,1,3,3,3-Hexaphenyldisiloxane (HPDS) was prepared.

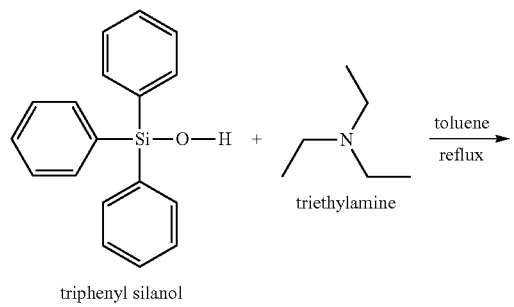

triphenyl silanol triethylamine

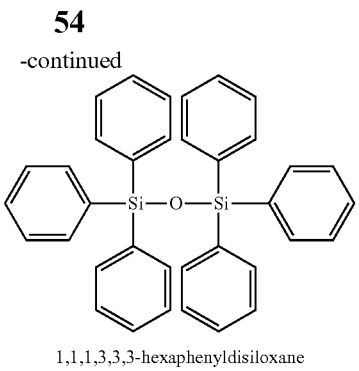

1,1,1,3,3,3-hexaphenyldisiloxane

To a stirred solution of 30 grams (0.11 mole) triphenylsilanol in 90 grams of toluene was added 11 grams triethylamine. The solution was heated to about 110° C. and stirred for 3 hours under toluene reflux. The reaction solution was cooled to ambient temperature during which the precipitation of as white solid was observed. The white solid was filtered and dried at 150° C. for 1 hour to remove toluene leaving 10 grams (34.4% of theory) of a white solid product, with 210° C. of melting point. The product was identified as 1,1,1,3,3,3-hexaphenyldisiloxane (HPDS) by 1H-NMR and 29Si-NMR analysis.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A flame retardant resin composition comprising (a) at least one resin which does not contain a triarylsilyloxy group, and (b) at least one triaryl silicon-containing compound of general formula (I):

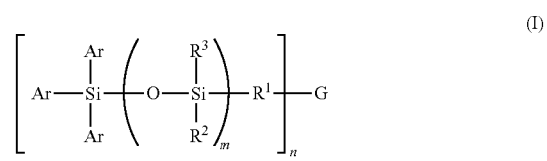

(I)

wherein each Ar independently is an unsubstituted aryl group of from about 6 to about 20 carbon atoms or substituted aryl group of from about 6 to about 20 carbon atoms; each $R^2$ and $R^3$ independently is a monovalent hydrocarbon group of from 1 to about 8 carbon atoms; each $R^1$ independently is a divalent saturated hydrocarbon group of from 1 to about 45 carbon atoms optionally containing one or more heteroatoms, or an alkenyl or alkynyl group up to 45 carbon atoms; G is hydrogen, a hydroxyl group, an acyclic organic group of from 1 to about 45 carbon atoms, a cyclic organic group of from 3 to about 20 carbon atoms, an acyclic or cyclic silicon-containing organic group of from 1 to about 50 carbon atoms optionally containing one or more heteroatoms, or a polymer moiety derived from a resin for which flame retardant capability is desired, G having a valence equal to subscript n; subscript m is from 1 to about 50; and, subscript n is from 1 to about 50.

2. The flame retardant resin composition of claim 1 wherein each $R^1$ is independently a divalent saturated hydrocarbon group of from 2 to about 45 carbon atoms.

3. The flame retardant resin composition of claim 1 wherein, in the triaryl silicon-containing compound (I), each Ar independently is an aryl group selected from the group consisting of phenyl, tolyl, xylyl, naphthyl, naphthalenyl, anthracenyl and phenanthryl.

4. The flame retardant resin composition of claim 1 wherein, in the triaryl silicon-containing compound (I), each Ar is phenyl.

5. The flame retardant resin composition of claim 1 wherein, in the triaryl silicon-containing compound (I), G is other than a polymer moiety and the at least one resin which does not contain the triarylsilyloxy group is selected from the group consisting of polyolefins, polycarbonates, polyesters, polyimides, polyamides, polystyrenes, polyurethanes, polyisocyanurates, polyepoxides, phenol formaldehyde resins, ABS terpolymer, SAN rubber, polyether ether ketone polymer, and mixtures thereof.

6. The flame retardant resin composition of claim 5 wherein the resin which does not contain a triarylsilyloxy group is a polycarbonate or polycarbonate-containing resin blend.

7. The flame retardant resin composition of claim 5 comprising at least one other flame retardant additive, wherein component (b) is present from about 10 to about 80 weight percent based on the total weight of component (b) and the at least one other flame retardant additive.

8. The flame retardant resin composition of claim 1 wherein, in triaryl silicon-containing compound (I), G is a polymer moiety derived from a resin selected from the group consisting of polyolefins, polycarbonates, polyesters, polyimides, polyamides, polystyrenes, polyurethanes, polyisocyanurates, polyepoxides, phenol formaldehyde resins, ABS terpolymer, SAN rubber, polyether ether ketone polymer, and mixtures thereof.

9. The flame retardant resin composition of claim 1 wherein, in the triaryl silicon-containing compound (I), each $R^1$ is a divalent alkyl radical of from 1 to about 45 carbon atoms.

10. The flame retardant resin composition of claim 1 wherein, in the triaryl silicon-containing compound (I), G is an alkoxysilyl group of the formula $-SiR^4_a(OR^5)_{3-a}$ wherein each occurrence of $R^4$ independently is a monovalent hydrocarbon group of from 1 to about 12 carbon atoms, each occurrence of $R^5$ independently is a monovalent hydrocarbon group of from 1 to about 50 carbon atoms optionally containing one or more heteroatoms, subscript a is 0 to 2 and, optionally, when subscript a is 0 or 1, two $R^5$ groups may be bonded together through a covalent bond to form a cyclized alkoxylsilyl group.

11. The flame retardant resin composition of claim 1, wherein component (b) is present from about 0.1 to about 60 weight percent, based on the total weight of components (a) and (b).

12. The flame retardant resin composition of claim 1 further comprising at least one flame retardant compound other than the triaryl silicon-containing compound (I).

13. The flame retardant resin composition of claim 1, wherein in the triaryl silicon-containing compound (I), subscript m is 1.

14. The flame retardant resin composition of claim 1, wherein in the triaryl silicon-containing compound (I), subscript m is from 2 to about 50.

15. The flame retardant resin composition of claim 1, wherein in the triaryl silicon-containing compound (I), G is selected from the group consisting of:

(a) an linear or branched acyclic organic group of up to about 45 carbon atom or cyclic organic group of from 3 to about 20 carbon atoms either of which is a saturated or unsaturated hydrocarbon radical optionally containing at least one of a heteroatom, carbonyl group, ester group, amide group or hydroxyl group, and having a valency of from 1 to about 25, subject to the limitation that the valence of the organic group is equal to the value of subscript n;

(b) a cyclic silicone of general formula (II):

$$\left[\begin{pmatrix} R^3 \\ | \\ -Si-O- \\ | \\ R^2 \end{pmatrix}_x \begin{pmatrix} (CH_2)_q \\ | \\ -Si-O- \\ | \\ R^2 \end{pmatrix}_y\right] \tag{II}$$

wherein:
each $R^2$ and $R^3$ independently is a monovalent hydrocarbon radical containing from 1 to about 8 carbon atoms; subscript q is an integer of from 1 to about 6, subscript x is 0 to about 8, and subscript y is an integer of from 1 to about 8, subject to the limitation that the value of subscript n=y;

(c) an acyclic silicone group of general formula (III):

$$M_b M^*_c D_d D^*_e T_f T^*_g Q_h A_i B_j C_k \tag{III}$$

wherein:
$M=R^4R^5R^6SiO_{1/2}$,
$M^*=R^4R^*R^6SiO_{1/2}$
$D=R^7R^8SiO_{2/2}$,
$D^*=R^7R^*SiO_{2/2}$
$T=R^9SiO_{3/2}$,
$T^*=R^*SiO_{3/2}$,
$Q=SiO_{4/2}$,
$A=O_{1/2}Si(R^{10})(R^{11})R^{12}Si(R^{13})(R^{14})O_{1/2}$
$B=O_{1/2}Si(R^{15})(R^{16})R^{17}Si(R^{18})O_{2/2}$
$C=O_{1/2}Si(R^{19})(R^{20})R^{21}SiO_{3/2}$
wherein:
$R^4, R^5, R^6, R^7, R^8, R^9, R^{10}, R^{11}, R^{13}, R^{14}, R^{15}, R^{16}, R^{18}, R^{19}$ and $R^{20}$ each independently is selected from the group consisting of $-OR^{22}$ and monovalent hydrocarbon radical containing from 1 to about 20 carbon atoms, optionally containing at least one of a heteroatom selected from the group consisting of oxygen, nitrogen and sulfur, an aromatic group of from 6 to about 10 carbon atoms, and a hydroxyl group; $R^{12}$, $R^{17}$ and $R^{21}$ are each independently a divalent hydrocarbon group of from 1 to about 8 carbon atoms; $R^{22}$ is a monovalent hydrocarbon of from 1 to about 20 carbon atoms, R* is a divalent hydrocarbon of from 1 to about 8 carbon atoms where one of the valences of R* is bound to $R^1$, and, subscripts b, c, d, e, f, g, h, i, j and k are zero or positive subject to the limitation b+c+d+e+f+g+h+i+j+k<1000, provided, c+e+g≥1;

(d) an alkoxysily group $-SiR^4_a(OR^5)_{3-a}$ wherein each occurrence of $R^4$ and $R^5$ is independently methyl, ethyl, propyl or isopropyl and a is 0 or 1, or cyclized alkoxysilyl group in which two $R^5$ groups are bonded together through a covalent bond; and, (e) a polymer moiety.

16. The flame retardant resin composition of claim 1 wherein in triaryl silicon-containing compound (I), each $R^1$ independently is a divalent alkyl group containing from 1 to about 6 carbon atoms.

17. The flame retardant resin composition of claim 1 wherein in triaryl silicon-containing compound (I), each $R^2$ and $R^3$ is methyl.

18. The flame retardant resin composition of claim 1 wherein in triaryl silicon-containing compound (I), G is a triarylsilyloxy group.

19. The flame retardant resin composition of claim 1 wherein, in the triaryl silicon-containing compound (I), $R^1$ is a divalent alkenyl or alkynyl group of from 2 to about 12 carbon atoms and G is hydrogen.

20. The flame retardant resin composition of claim 1 wherein the triaryl silicon-containing compound (I) is at least one compound selected from the group consisting of:

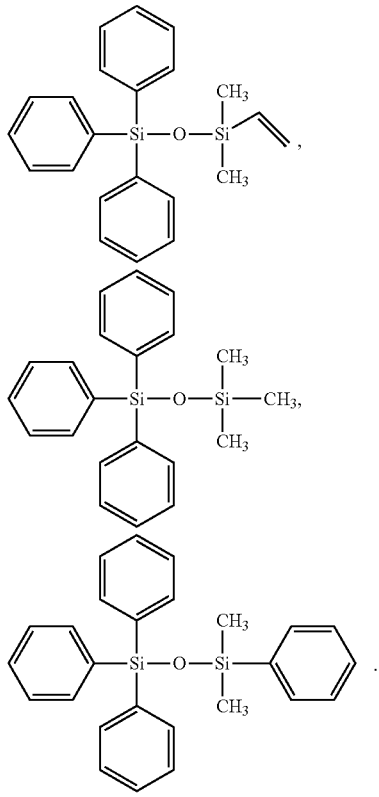

21. The flame retardant resin composition of claim 1 wherein the triaryl silicon-containing compound (I) is selected from the group consisting of:

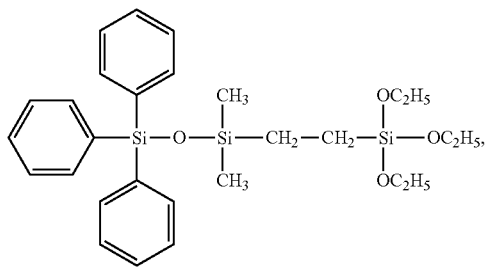

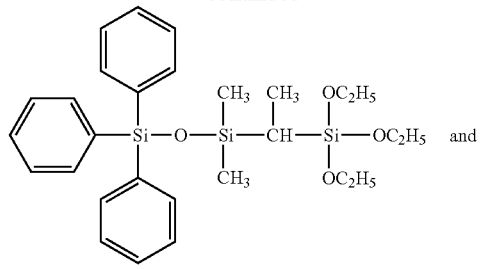

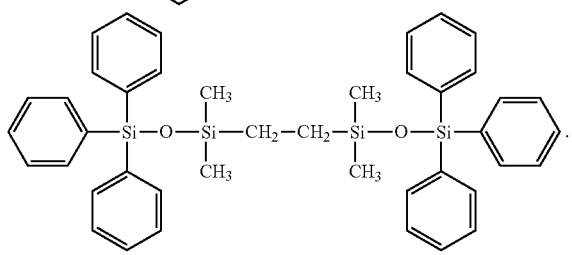

22. The flame retardant resin composition of claim 1 wherein the triaryl silicon containing compound (I) has general formula (I):

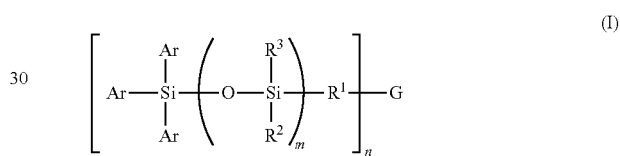

wherein each Ar independently is an unsubstituted aryl group of from about 6 to about 20 carbon atoms or substituted aryl group of from about 6 to about 20 carbon atoms; each $R^2$ and $R^3$ independently is a monovalent hydrocarbon group of from 1 to about 8 carbon atoms; each $R^1$ independently is a divalent saturated hydrocarbon group of from 1 to about 45 carbon atoms optionally containing one or more heteroatoms or an alkenyl or alkynyl group up to 45 carbon atoms; G is an alkoxysilyl group $—SiR^4_a(OR^5)_{3-a}$, wherein each occurrence of $R^4$ is independently a monovalent hydrocarbon group of from 1 to about 12 carbon atoms; each occurrence of $R^5$ independently is a monovalent hydrocarbon of from 1 to about 50 carbon atoms, an organic group derived from a resin having more than 30 carbon atoms and selected from the group consisting of polycarbonates, polyacetals, polyesters, polysulfones, polyamides, polyimides, polyetherimides, polyetherether ketones, polystyrenes, polyurethanes, polyisocyanurates, polyepoxides, phenol formaldehyde resins, polyphenylene oxides, polyphenylene sulfides, polylactides, polyolefins, styrene-ethylene-butylene-butylenes (STEBS) copolymer, acrylics, acrylonitrile butadiene styrene (ABS) terpolymers, styrene acrylonitrile (SAN) rubbers, acetals, polyimidazoles, polytetrafluoroethylene (TPFE), polyvinyl chloride (PVC) and polyvinylidene chloride, where a carbon atom of the $R^5$ group is bonded to the oxygen atom of the $—OR^5$ group, or a cyclized alkoxysilyl group in which two $R^5$ groups, when present, are bonded together through a covalent bond, subscript m is from 1 to about 50 and the subscript n is 1.

23. The flame retardant resin composition of claim 22, wherein said composition further comprises a condensation catalyst.

24. The flame retardant resin composition of claim 23, wherein the condensation catalyst is a tin salt.

25. The flame retardant resin composition of claim 1, wherein the triaryl silicon-containing compound (I) has the general formula (I):

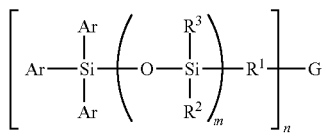
(I)

wherein each Ar independently is an unsubstituted aryl group of from about 6 to about 20 carbon atoms or a substituted aryl group of from about 6 to about 20 carbon atoms; $R^2$ and $R^3$ each independently is selected from a monovalent hydrocarbon group of from 1 to about 8 carbon atoms; each $R^1$ is independently a divalent saturated hydrocarbon group of from 1 to about 45 carbon atoms optionally containing one or more heteroatoms or an alkenyl or alkynyl group up to 45 carbon atoms; G is an organic group having a valence equal to subscript n, the subscript a is 0 to 2, and each of subscripts m and n independently being from 1 to about 50, with the provisos that (i) when m is equal to 1 and $R^1$ is a divalent saturated hydrocarbon group of form 1 to about 45 carbon atom or an alkenyl or alkynyl group up to 45 carbon atoms, then G is an alkoxysilyl group —$SiR^4_a(OR^5)_{3-a}$, wherein each occurrence of $R^4$ is independently a monovalent hydrocarbon group of from 1 to about 12 carbon atoms; each occurrence of $R^5$ independently is a monovalent hydrocarbon of from 1 to about 50 carbon atoms, an organic group derived from a resin having more than 30 carbon atoms and selected from the group consisting of polycarbonates, polyacetals, polyesters, polysulfones, polyamides, polyimides, polyetherimides, polyetheretherketones, polystyrenes, polyurethanes, polyisocyanurates, polyepoxides, phenol formaldehyde resins, polyphenylene oxides, polyphenylene sulfides, polylactides, polyolefins, styrene-ethylene-butylene-butylenes (STEBS) copolymer, acrylics, acrylonitrile butadiene styrene (ABS) terpolymers, styrene acrylonitrile (SAN) rubbers, acetals, polyimidazoles, polytetrafluoroethylene (TPFE), polyvinyl chloride (PVC) and polyvinylidene chloride, where a carbon atom of the $R^5$ group is bonded to the oxygen atom of the —$OR^5$ group, or a cyclized alkoxysilyl group in which two $R^5$ groups, when present, are bonded together through a covalent bond, and (ii) when m is 2 to 50, then G is selected from the group consisting of:
(a) a linear or branched acyclic organic group having up to about 45 carbon atom or a cyclic organic group of from 3 to about 20 carbon atoms either of which is a saturated or unsaturated hydrocarbon radical and optionally containing at least one of a heteroatom, carbonyl group, ester group, amide group or hydroxyl group, and having a valence of from 1 to about 25, subject to the requirement that the valance of the organic group is equal to the value of subscript n;
(b) a cyclic silicone of general formula (II):

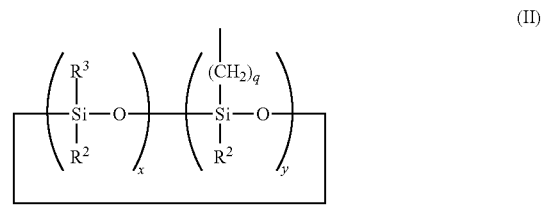
(II)

wherein:
each $R^2$ and $R^3$ independently is a monovalent hydrocarbon radical containing from 1 to about 8 carbon atoms; subscript q is an integer of from 1 to about 6, subscript x is 0 to about 8, and subscript y is an integer of from 1 to about 8, subject to the requirement that the value of subscript n=y;
(c) an acyclic silicone group of general formula (III):

$$M_b M^*_c D_d D^*_e T_f T^*_g Q_h A_i B_j C_k \quad (III)$$

wherein:
$M = R^4 R^5 R^6 SiO_{1/2}$,
$M^* = R^4 R^* R^6 SiO_{1/2}$,
$D = R^7 R^8 SiO_{2/2}$,
$D^* = R^7 R^* SiO_{2/2}$,
$T = R^9 SiO_{3/2}$,
$T^* = R^* SiO_{3/2}$,
$Q = SiO_{4/2}$,
$A = O_{1/2} Si(R^{10})(R^{11}) R^{12} Si(R^{13})(R^{14}) O_{1/2}$
$B = O_{1/2} Si(R^{15})(R^{16}) R^{17} Si(R^{18}) O_{2/2}$
$C = O_{1/2} Si(R^{19})(R^{20}) R^{21} SiO_{3/2}$
wherein:
$R^4$, $R^5$, $R^6$, $R^7$, $R^8$, $R^9$, $R^{10}$, $R^{11}$, $R^{13}$, $R^{14}$, $R^{15}$, $R^{16}$, $R^{18}$, $R^{19}$ and $R^{20}$ each independently is selected from the group consisting of $OR^{22}$ and monovalent hydrocarbon radical containing from 1 to about 20 carbon atoms, optionally containing at least one of a heteroatom, an aromatic group of from 6 to 10 carbon atoms, and a hydroxyl group; $R^{12}$, $R^{17}$ and $R^{21}$ each independently is a divalent hydrocarbon group of from 1 to about 8 carbon atoms; $R^{22}$ is a monovalent hydrocarbon group of from 1 to about 20 carbon atoms; $R^*$ is a divalent hydrocarbon of from 1 to about 8 carbon atoms, where one of the valences of $R^*$ is bound to $R^1$; and, subscripts b, c, d, e, f, g, h, i, j and k are zero or positive subject to the requirement that $b+c+d+e+f+g+h+i+j+k<1000$, provided, $c+e+g \geq 1$;
(d) an alkoxysilyl group —$R^* SiR^4_a (OR^5)_{3-a}$, wherein each occurrence of $R^*$ is a divalent hydrocarbon of from 1 to about 8 carbon atoms, $R^4$ is independently a monovalent hydrocarbon group of from 1 to about 12 carbon atoms; each occurrence of $R^5$ independently is a monovalent hydrocarbon of from 1 to about 50 carbon atoms, an organic group derived from a resin having more than 30 carbon atoms and selected from the group consisting of polycarbonates, polyacetals, polyesters, polysulfones, polyamides, polyimides, polyetherimides, polyetherether ketones, polystyrenes, polyurethanes, polyisocyanurates, polyepoxides, phenol formaldehyde resins, polyphenylene oxides, polyphenylene sulfides, polylactides, polyolefins, styrene-ethylene-butylene-butylenes (STEBS) copolymer, acrylics, acrylonitrile butadiene styrene (ABS) terpolymers, styrene acrylonitrile (SAN) rubbers, acetals, polyimidazoles, polytetrafluoroethylene (TPFE), polyvinyl chloride (PVC) and polyvinylidene chloride, where a carbon atom of the $R^5$ group is bonded to the oxygen atom of the $—OR^5$ group, or a cyclized alkoxysilyl group in which two $R^5$ groups, when present, are bonded together through a covalent bond; and, (e) a polymer moiety.

26. A triaryl silicon-containing compound of general formula (I):

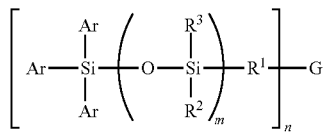

(I)

wherein each Ar independently is an unsubstituted aryl group of from about 6 to about 20 carbon atoms or a substituted aryl group of from about 6 to about 20 carbon atoms; $R^2$ and $R^3$ each independently is selected from a monovalent hydrocarbon group of from 1 to about 8 carbon atoms; each $R^1$ is independently a divalent saturated hydrocarbon group of from 1 to about 45 carbon atoms optionally containing one or more heteroatoms or an alkenyl or alkynyl group up to 45 carbon; G is an organic group having a valence equal to subscript n, the subscript a is 0 to 2, and each of subscripts m and n independently being from 1 to about 50, with the provisos that (i) when m is equal to 1 and $R^1$ is a divalent saturated hydrocarbon group of from 1 to about 45 carbon atom heteroatoms or an alkenyl or alkynyl group up to 45 carbon atoms, then G is an alkoxysilyl group $—SiR^4_a(OR^5)_{3-a}$, wherein each occurrence of $R^4$ is independently a monovalent hydrocarbon group of from 1 to about 12 carbon atoms; each occurrence of $R^5$ independently is a monovalent hydrocarbon of from 1 to about 50 carbon atoms, an organic group derived from a resin having more than about 30 carbon atoms and selected from the group consisting of polycarbonates, polyacetals, polyesters, polysulfones, polyamides, polyimides, polyetherimides, polyetherether ketones, polystyrenes, polyurethanes, polyisocyanurates, polyepoxides, phenol formaldehyde resins, polyphenylene oxides, polyphenylene sulfides, polylactides, polyolefins, styrene-ethylene-butylene-butylenes (STEBS) copolymer, acrylics, acrylonitrile butadiene styrene (ABS) terpolymers, styrene acrylonitrile (SAN) rubbers, acetals, polyimidazoles, polytetrafluoroethylene (TPFE), polyvinyl chloride (PVC) and polyvinylidene chloride, where a carbon atom of the $R^5$ group is bonded to the oxygen atom of the $—OR^5$ group, or a cyclized alkoxysilyl group in which two $R^5$ groups, when present, are bonded together through a covalent bond, and (ii) when m is 2 to about 50, G is selected from the group consisting of:

(a) a linear or branched acyclic organic group having up to about 45 carbon atom or a cyclic organic group of from 3 to about 20 carbon atoms either of which is a saturated or unsaturated hydrocarbon radical optionally containing at least one of a heteroatom, carbonyl group, ester group, amide group or hydroxyl group, and having a valence of from 1 to about 25, subject to the requirement that the valence of the organic group is equal to the value of subscript n;

(b) a cyclic silicone of general formula (II):

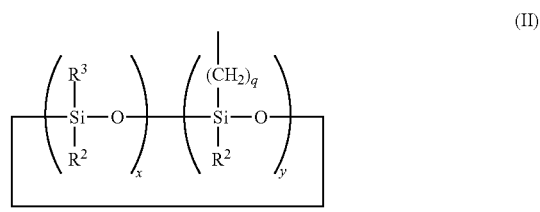

(II)

wherein:
each $R^2$ and $R^3$ independently is a monovalent hydrocarbon radical containing from 1 to about 8 carbon atoms; subscript q is an integer of from 1 to about 6, subscript x is 0 to about 8, and subscript y is an integer of from 1 to about 8, subject to the requirement that the value of subscript n=y;

(c) an acyclic silicone group of general formula (III):

$$M_b M^*_c D_d D^*_e T_f T^*_g Q_h A_i B_j C_k \quad (III)$$

wherein:
$M=R^4R^5R^6SiO_{1/2}$,
$M^*=R^4R^*R^6SiO_{1/2}$
$D=R^7R^8SiO_{2/2}$,
$D^*=R^7R^*SiO_{2/2}$
$T=R^9SiO_{3/2}$,
$T^*=R^*SiO_{3/2}$,
$Q=SiO_{4/2}$,
$A=O_{1/2}Si(R^{10})(R^{11})R^{12}Si(R^{13})(R^{14})O_{1/2}$
$B=O_{1/2}Si(R^{15})(R^{16})R^{17}Si(R^{18})O_{2/2}$
$C=O_{1/2}Si(R^{19})(R^{20})R^{21}SiO_{3/2}$
wherein:
$R^4$, $R^5$, $R^6$, $R^7$, $R^8$, $R^9$, $R^{10}$, $R^{11}$, $R^{13}$, $R^{14}$, $R^{15}$, $R^{16}$, $R^{18}$, $R^{19}$ and $R^{20}$ each independently is selected from the group consisting of $OR^{22}$ and monovalent hydrocarbon radical containing from 1 to about 20 carbon atoms, optionally containing at least one of a heteroatom, an aromatic group of from 6 to 10 carbon atoms, and a hydroxyl group; $R^{12}$, $R^{17}$ and $R^{21}$ each independently is a divalent hydrocarbon group of from 1 to about 8 carbon atoms; $R^{22}$ is a monovalent hydrocarbon group of from 1 to about 20 carbon atoms; $R^*$ is a divalent hydrocarbon of from 1 to about 8 carbon atoms, where one of the valences of $R^*$ is bound to $R^1$; and, subscripts b, c, d, e, f, g, h, i, j and k are zero or positive subject to the requirement that b+c+d+e+f+g+h+i+j+k<1000, provided, c+e+g≥1;

(d) an alkoxysilyl group $—R^*SiR^4_a(OR^5)_{3-a}$, wherein each occurrence of $R^*$ is a divalent hydrocarbon of from 1 to about 8 carbon atoms, $R^4$ is independently a monovalent hydrocarbon group of from 1 to about 12 carbon atoms; each occurrence of $R^5$ independently is a monovalent hydrocarbon of from 1 to about 50 carbon atoms, an organic group derived from a resin having more than 30 carbon atoms and selected from the group consisting of polycarbonates, polyacetals, polyesters, polysulfones, polyamides, polyimides, polyetherimides, polyetherether ketones, polystyrenes, polyurethanes, polyisocyanurates, polyepoxides, phenol formaldehyde resins, polyphenylene oxides, polyphenylene sulfides, polylactides, polyolefins, styrene-ethylene-butylene-butylenes (STEBS) copolymer, acrylics, acrylonitrile butadiene styrene (ABS) terpolymers, styrene acrylonitrile (SAN) rubbers, acetals, polyimidazoles, polytetrafluoroethylene (TPFE), polyvinyl chloride (PVC) and polyvinylidene chloride, where a carbon atom of the $R^5$ group is bonded to the oxygen atom of the $-OR^5$ group, or a cyclized alkoxysilyl group in which two $R^5$ groups, when present, are bonded together through a covalent bond; and, (e) a polymer moiety.

27. The triaryl silicon-containing compound (I) of claim 26 wherein each Ar independently is an aryl group selected from the group consisting of phenyl, tolyl, xylyl, naphthyl, naphthalenyl, anthracenyl and phenanthryl.

28. The triaryl silicon-containing compound (I) of claim 27 wherein each Ar is phenyl.

29. The triaryl silicon-containing compound (I) of claim 26 wherein each $R^1$ is a divalent alkyl radical of up to about 45 carbon atoms.

30. The triaryl silicon-containing compound (II) of claim 26 of the general formula:

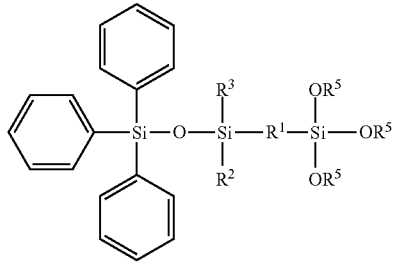

wherein $R^1$, $R^2$, $R^3$, $R^4$ and $R^5$ are as previously defined.

31. The triaryl silicon-containing compound (II) of claim 26 of the formula:

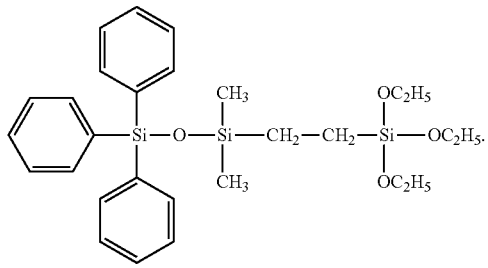 [SMILES: CCO[Si](CC[Si](C)(C)O[Si](c1ccccc1)(c1ccccc1)c1ccccc1)(OCC)OCC]

32. The triaryl silicon-containing compound (I) of claim 26 wherein each Ar independently is an unsubstituted aryl group of from about 6 to about 20 carbon atoms or substituted aryl group of from about 6 to about 20 carbon atoms; $R^2$ and $R^3$ each independently is a monovalent hydrocarbon group of from 1 to about 8 carbon atoms; each $R^1$ is independently a divalent saturated or hydrocarbon group of from 1 to about 45 carbon atoms optionally containing one or more heteroatoms or an alkenyl or alkynyl group up to 45 carbon atoms;

G is selected from the group consisting of:
(a) a cyclic silicone of general formula (II):

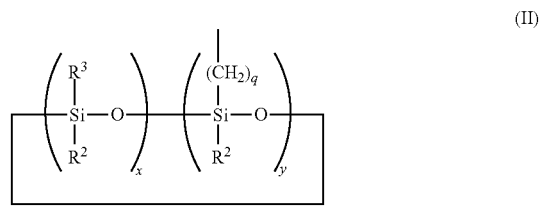

wherein:
each $R^2$ and $R^3$ independently is a monovalent hydrocarbon radical containing from 1 to about 8 carbon atoms; subscript q is an integer of from 1 to about 6, subscript x is 0 to about 8, and subscript y is an integer of from 1 to about 8, subject to the limitation that the value of subscript n=y;

(b) an acyclic silicone group of general formula (III):

wherein:
$M=R^4R^5R^6SiO_{1/2}$,
$M^*=R^4R^*R^6SiO_{1/2}$
$D=R^7R^8SiO_{2/2}$,
$D^*=R^7R^*SiO_{2/2}$
$T=R^9SiO_{3/2}$,
$T^*=R^*SiO_{3/2}$,
$Q=SiO_{4/2}$,
$A=O_{1/2}Si(R^{10})(R^{11})R^{12}Si(R^{13})(R^{14})O_{1/2}$
$B=O_{1/2}Si(R^{15})(R^{16})R^{17}Si(R^{18})O_{2/2}$
$C=O_{1/2}Si(R^{19})(R^{20})R^{21}SiO_{3/2}$
wherein:
$R^4$, $R^5$, $R^6$, $R^7$, $R^8$, $R^9$, $R^{10}$, $R^{11}$, $R^{13}$, $R^{14}$, $R^{15}$, $R^{16}$, $R^{18}$, $R^{19}$ and $R^{20}$ each independently is selected from the group consisting of $OR^{22}$ and monovalent hydrocarbon radical containing from 1 to about 20 carbon atoms optionally containing at least one of a heteroatom, an aromatic group of from 6 to 10 carbon atoms and a hydroxyl group; $R^{12}$, $R^{17}$ and $R^{21}$ each independently is a divalent hydrocarbon group of from 1 to about 8 carbon atoms; $R^{22}$ is a monovalent hydrocarbon of from 1 to about 20 carbon atoms; $R^*$ is a divalent hydrocarbon of from 1 to about 8 carbon atoms, where one of the valences of $R^*$ is bound to R'; and, subscripts b, c, d, e, f, g, h, i, j and k are zero or positive subject to the limitation b+c+d+e+f+g+h+i+j<1000 with the lower endpoints of any of said ranges of b+c+d+e+f+g+h+i+j being any one or more of 1, 2, 3, 5, 10, 12, 20, 50 or 60, provided, c+e+g≥1 with upper end points of such ranges of c+e+g being any one of 4, 5, 8, 10, 12, 20, 50, 60 or 100;

(c) an alkoxysilyl group $-R^*SiR^4_a(OR^5)_{3-a}$, wherein each occurrence of $R^*$ is a divalent hydrocarbon of from 1 to about 8 carbon atoms, $R^4$ is independently a monovalent hydrocarbon group of from 1 to about 12 carbon atoms; each occurrence of $R^5$ independently is a monovalent hydrocarbon of from 1 to about 50 carbon atoms, an organic group derived from a resin having more than 30 carbon atoms and selected from the group consisting of polycarbonates, polyacetals, polyesters, polysulfones, polyamides, polyimides, polyetherimides, polyetherether ketones, polystyrenes, polyurethanes, polyisocyanurates, polyepoxides, phenol formaldehyde resins, polyphenylene oxides, polyphenylene sulfides, polylactides, polyolefins, styrene-ethylene-butylene-butylenes (STEBS) copolymer, acrylics, acrylonitrile butadiene styrene (ABS) terpolymers, styrene acrylonitrile (SAN) rubbers, acetals, polyimidazoles, polytetrafluoroethylene (TPFE), polyvinyl chloride (PVC) and polyvinylidene chloride, where a carbon atom of the $R^5$ group is bonded to the oxygen atom of the —$OR^5$ group, or a cyclized alkoxysilyl group in which two $R^5$ groups, when present, are bonded together through a covalent bond; and, (d) a polymer moiety, subscript m being an integer of from 2 to about 50.

33. The triaryl silicon-compound (I) of claim 32, where $R^5$ is an organic group derived from polycarbonate.

34. The triaryl silicon-containing compound (I) of claim 26 wherein G is an alkoxysilyl group —$SiR^4{}_a(OR^5)_{3-a}$ wherein each occurrence of $R^4$ is independently a monovalent hydrocarbon group of from 1 to about 12 carbon atoms; each occurrence of $R^5$ independently is a monovalent hydrocarbon of from 1 to about 50 carbon atoms, an organic group derived from a resin having more than about 30 carbon atoms and selected from the group consisting of polycarbonates, polyacetals, polyesters, polysulfones, polyamides, polyimides, polyetherimides, polyetherether ketones, polystyrenes, polyurethanes, polyisocyanurates, polyepoxides, phenol formaldehyde resins, polyphenylene oxides, polyphenylene sulfides, polylactides, polyolefins, styrene-ethylene-butylene-butylenes (STEBS) copolymer, acrylics, acrylonitrile butadiene styrene (ABS) terpolymers, styrene acrylonitrile (SAN) rubbers, acetals, polyimidazoles, polytetrafluoroethylene (TPFE), polyvinyl chloride (PVC) and polyvinylidene chloride, where a carbon atom of the $R^5$ group is bonded to the oxygen atom of the —$OR^5$ group, or a cyclized alkoxysilyl group in which two $R^5$ groups, when present, are bonded together through a covalent bond, m is 1, and $R^1$ is a divalent saturated hydrocarbon group of from 1 to about 45 carbon atoms or an alkenyl or alkynyl group up to 45 carbon atoms.

\* \* \* \* \*